(12) United States Patent
Rawls et al.

(10) Patent No.: US 8,785,514 B2
(45) Date of Patent: Jul. 22, 2014

(54) DUAL-CURE DENTAL RESINS AND ADHESIVES WITH INCREASED CURE AND COLOR STABILITY AND LOW COLOR

(75) Inventors: H. Ralph Rawls, San Antonio, TX (US);
Kyumin Whang, San Antonio, TX (US);
Nasser Barghi, San Antonio, TX (US);
Dong-Hoon Shin, Cheonan (KR);
Richard Plymale, Davison, MI (US);
Janice Plymale, legal representative, Davison, MI (US)

(73) Assignee: The Board of Regents of The University of Texas System, Austin, TX (US)

( * ) Notice: Subject to any disclaimer, the term of this patent is extended or adjusted under 35 U.S.C. 154(b) by 333 days.

(21) Appl. No.: 12/745,423

(22) PCT Filed: Nov. 28, 2008

(86) PCT No.: PCT/US2008/085067
§ 371 (c)(1),
(2), (4) Date: Jan. 25, 2011

(87) PCT Pub. No.: WO2009/073570
PCT Pub. Date: Jun. 11, 2009

(65) Prior Publication Data
US 2011/0200973 A1 Aug. 18, 2011

Related U.S. Application Data

(60) Provisional application No. 60/991,195, filed on Nov. 29, 2007.

(51) Int. Cl.
| | | |
|---|---|---|
| C08G 59/68 | (2006.01) |
| C08G 61/04 | (2006.01) |
| C08B 37/00 | (2006.01) |
| C08F 2/50 | (2006.01) |
| C08F 2/46 | (2006.01) |
| C08F 2/48 | (2006.01) |
| C04B 35/571 | (2006.01) |
| B29C 71/04 | (2006.01) |

(52) U.S. Cl.
USPC ............ 522/15; 522/12; 522/7; 522/6; 522/1; 522/8; 522/13; 522/21; 522/22; 522/71; 520/1

(58) Field of Classification Search
USPC ............. 522/15, 12, 7, 6, 1, 8, 13, 21, 22, 71; 520/1
See application file for complete search history.

(56) References Cited

U.S. PATENT DOCUMENTS

| | | | | | |
|---|---|---|---|---|---|
| 3,991,008 | A | * | 11/1976 | Temin et al. | 523/115 |
| 4,751,138 | A | * | 6/1988 | Tumey et al. | 428/323 |
| 6,084,004 | A | * | 7/2000 | Weinmann et al. | 522/25 |
| 6,306,926 | B1 | * | 10/2001 | Bretscher et al. | 523/116 |
| 6,458,865 | B2 | * | 10/2002 | Chappelow et al. | 522/14 |
| 6,765,036 | B2 | * | 7/2004 | Dede et al. | 522/15 |
| 6,982,288 | B2 | * | 1/2006 | Mitra et al. | 523/120 |
| 2003/0157357 | A1 | * | 8/2003 | Rusin et al. | 428/542.8 |
| 2005/0113477 | A1 | * | 5/2005 | Oxman et al. | 522/6 |

OTHER PUBLICATIONS

He, J.-H., "Synergistic Effects of aminies on the intra-ion pair electron transfer dye photosensitization system Eo(IPh2)2", J. Photochem. Photobiol. A: Chemistry, 89(3) pp. 229-234, Aug. 2, 1995.

* cited by examiner

Primary Examiner — Ling Choi
Assistant Examiner — Jessica E Whiteley
(74) Attorney, Agent, or Firm — Winstead PC

(57) ABSTRACT

Various embodiments of the present invention generally relate to a light-cure and dual-cure resin that have low color and is color stable over conventional light, self and dual-cured resins. Additionally, the light-cure resin has enhanced degree of cure over conventional light-cure resins. Finally, due to the low color and enhanced color stability of the dual-cure resins, their inherent property of having lower shrinkage stress as compared to light-cure resins can now be utilized in various dental applications and other resin applications.

11 Claims, 23 Drawing Sheets

Figure 1

Experimental groups for degree and rate of conversion

| Components and proportion by weight | Code | |
|---|---|---|
| | *1%* | *3%* |
| CQ only | 1C | 3C |
| 1 part of CQ and 2 parts of OPPI | 1CO | 3CO |
| 1 part of CQ and 2 parts of DMAEMA | 1CA | 3CA |
| Equally proportioned CQ, OPPI, and DMAEMA | 1COA | 3COA |

Figure 2

Degree of conversion (%) of GTE with various photoinitiators

| Curing time (sec.) Groups | *5 s* | *20 s* | *40 s* | *60 s* | *300 s* |
|---|---|---|---|---|---|
| 1C | 0.33 | 0.00 | 0.83 | 0.96 | 3.36 |
| 1CO | 7.17 | 9.27 | 12.66 | 15.81 | 39.73 |
| 1CA | 6.02 | 20.11 | 40.65 | 49.96 | 56.93 |
| 1COA | 13.24 | 32.08 | 43.95 | 48.24 | 53.64 |
| 3C | 0.79 | 2.51 | 2.56 | 4.33 | 23.57 |
| 3CO | 7.34 | 17.04 | 35.45 | 48.10 | 57.46 |
| 3CA | 0.8 | 4.88 | 19.52 | 41.21 | 52.12 |
| 3COA | 51.11 | 56.86 | 58.28 | 63.99 | 66.24 |

Degree of conversion of GTE with various photoinitiators *vs.* exposure time

Rate of initial conversion (% conversion/sec) of GTE with various photoinitiators

Figure 5
Color coordinates

| Groups | Storage conditions | Baseline L* | Baseline a* | Baseline b* | Week 1 L* | Week 1 a* | Week 1 b* | Week 2 L* | Week 2 a* | Week 2 b* | Week 4 L* | Week 4 a* | Week 4 b* |
|---|---|---|---|---|---|---|---|---|---|---|---|---|---|
| 3CO | Room, wet | 87.29 | -3.82 | 15.96 | 87.11 | -3.87 | 16.97 | 86.75 | -3.98 | 18.61 | 86.49 | -3.82 | 19.26 |
|  | 60 C, wet | 87.17 | -3.85 | 16.06 | 87.05 | -4.24 | 21.59 | 87.17 | -4.17 | 20.99 | 86.93 | -4.24 | 21.34 |
|  | Room, dry | 87.17 | -3.97 | 16.50 | 86.70 | -4.23 | 18.34 | 86.63 | -4.27 | 18.83 | 86.31 | -4.31 | 19.22 |
|  | 60 C, dry | 87.17 | -3.94 | 16.48 | 86.19 | -4.61 | 24.21 | 86.56 | -4.64 | 23.33 | 86.68 | -4.74 | 23.51 |
| 3CA | Room, wet | 84.30 | -1.06 | 27.86 | 82.99 | 0.78 | 32.49 | 83.75 | 0.66 | 31.81 | 84.28 | 0.20 | 32.23 |
|  | 60 C, wet | 84.09 | -1.01 | 27.97 | 84.39 | -1.73 | 31.72 | 84.62 | -1.75 | 30.94 | 84.66 | -1.91 | 29.92 |
|  | Room, dry | 84.10 | -0.94 | 28.11 | 82.29 | 0.26 | 33.38 | 82.03 | 0.48 | 34.71 | 81.74 | 0.59 | 35.21 |
|  | 60 C, dry | 84.17 | -0.99 | 27.88 | 83.61 | -0.93 | 36.37 | 84.12 | -2.14 | 34.90 | 83.79 | -2.41 | 35.55 |
| 3COA | Room, wet | 86.89 | -3.37 | 16.60 | 86.12 | -3.41 | 19.75 | 86.09 | -3.28 | 19.79 | 86.66 | -2.91 | 18.24 |
|  | 60 C, wet | 86.77 | -3.96 | 18.39 | 86.96 | -4.05 | 23.99 | 86.65 | -3.64 | 23.86 | 86.31 | -3.45 | 24.62 |
|  | Room, dry | 86.83 | -3.74 | 17.56 | 85.88 | -3.75 | 21.21 | 85.48 | -3.80 | 22.18 | 85.16 | -3.58 | 22.65 |
|  | 60 C, dry | 86.94 | -3.95 | 18.31 | 86.88 | -4.96 | 25.44 | 86.51 | -4.6 | 25.96 | 86.40 | -4.85 | 26.37 |
| 1CA | Room, wet | 87.03 | -1.75 | 13.67 | 86.33 | -0.22 | 15.14 | 86.52 | 0.02 | 14.80 | 86.72 | 0.02 | 14.58 |
|  | 60 C, wet | 87.07 | -1.75 | 13.61 | 87.33 | -1.78 | 15.75 | 86.97 | -1.68 | 15.66 | 86.91 | -1.60 | 15.45 |
|  | Room, dry | 87.09 | -1.76 | 13.58 | 85.84 | -0.72 | 15.93 | 85.61 | -0.66 | 16.28 | 85.51 | -0.62 | 16.77 |
|  | 60 C, dry | 87.12 | -1.71 | 13.47 | 87.08 | -2.69 | 16.61 | 87.16 | -2.66 | 16.03 | 87.23 | -2.65 | 15.60 |
| 1COA | Room, wet | 88.11 | -1.97 | 9.81 | 87.88 | -1.53 | 10.55 | 87.84 | -1.24 | 10.41 | 87.81 | -1.00 | 10.37 |
|  | 60 C, wet | 88.11 | -2.13 | 10.08 | 87.77 | -1.42 | 12.59 | 87.44 | -1.37 | 12.76 | 87.42 | -1.36 | 12.92 |
|  | Room, dry | 88.05 | -2.12 | 10.34 | 87.47 | -2.05 | 11.61 | 87.17 | -2.00 | 11.74 | 87.12 | -1.94 | 11.83 |
|  | 60 C, dry | 88.10 | -2.13 | 10.23 | 87.77 | -1.82 | 11.97 | 87.66 | -2.03 | 12.41 | 87.68 | -2.06 | 12.44 |

Figure 6
Color change ($\Delta E$) -- Mean (S.D.)

| Groups | Storage conditions | Week 1 | Week 2 | Week 4 |
|---|---|---|---|---|
| 3CO | Room, wet | 1.03 (1.27) | 2.71 (1.17) | 3.40 (1.65) |
|  | 60 C, wet | 5.54 (1.53) | 4.94 (1.67) | 5.30 (0.92) |
|  | Room, dry | 1.91 (1.42) | 2.41 (1.73) | 2.87 (1.73) |
|  | 60 C, dry | 7.82 (0.30) | 6.92 (0.67) | 7.09 (0.74) |
| 3CA | Room, wet | 5.16 (0.28) | 4.35 (1.05) | 4.56 (0.35) |
|  | 60 C, wet | 3.83 (0.38) | 3.11 (0.49) | 2.23 (0.47) |
|  | Room, dry | 5.70 (0.95) | 7.06 (0.57) | 7.64 (0.60) |
|  | 60 C, dry | 8.51 (0.23) | 7.12 (1.20) | 7.81 (1.45) |
| 3COA | Room, wet | 3.25 (0.88) | 3.29 (0.67) | 1.72 (0.84) |
|  | 60 C, wet | 5.61 (1.48) | 5.48 (1.44) | 6.27 (1.35) |
|  | Room, dry | 3.76 (1.71) | 4.81 (1.70) | 5.36 (0.62) |
|  | 60 C, dry | 7.20 (2.12) | 7.72 (0.87) | 8.13 (0.33) |
| 1CA | Room, wet | 2.23 (0.29) | 2.16 (0.24) | 2.02 (0.10) |
|  | 60 C, wet | 2.15 (0.39) | 2.05 (0.51) | 1.85 (0.52) |
|  | Room, dry | 2.86 (0.13) | 3.28 (0.55) | 3.74 (0.55) |
|  | 60 C, dry | 3.29 (0.46) | 2.73 (0.38) | 2.33 (0.31) |
| 1COA | Room, wet | 0.89 (0.78) | 0.99 (0.53) | 1.16 (0.47) |
|  | 60 C, wet | 2.63 (0.55) | 2.86 (0.53) | 3.02 (0.30) |
|  | Room, dry | 1.40 (1.13) | 1.66 (0.87) | 1.77 (0.19) |
|  | 60 C, dry | 1.80 (1.13) | 2.23 (1.21) | 2.26 (1.45) |

Change of ΔE values with room, wet condition

Change of ΔE values with 60 C, wet conditions

Change of ΔE values with room, dry conditions

Change of ΔE values with 60 C, dry conditions

Change of b* values with room temperature and wet conditions

Change of b* values with high temperature and wet conditions

Change of b* values with room temperature and dry conditions

Change of b* values with high temperature and dry conditions

Figure 15

Composition of GTE-based groups for OPPI vs. no OPPI analysis

| | Resin Composition | | | | | Total Composition | | |
|---|---|---|---|---|---|---|---|---|
| | CQ | PPD | DMAEMA | GTE | OPPI | Resin | TS-530 Filler | Treated Foundation Filler |
| GTE1 | 0% | 1% | 2% | 97% | 0% | 25% | 5% | 70% |
| GTE2 | 0.25% | 0.75% | 2% | 97% | 0% | 25% | 5% | 70% |
| GTE3 | 0.50% | 0.50% | 2% | 97% | 0% | 25% | 5% | 70% |
| GTE4 | 0.75% | 0.25% | 2% | 97% | 0% | 25% | 5% | 70% |
| GTE5 | 1% | 0% | 2% | 97% | 0% | 25% | 5% | 70% |
| OGTE1 | 0% | 1% | 2% | 96% | 1% | 25% | 5% | 70% |
| OGTE2 | 0.25% | 0.75% | 2% | 96% | 1% | 25% | 5% | 70% |
| OGTE3 | 0.50% | 0.50% | 2% | 96% | 1% | 25% | 5% | 70% |
| OGTE4 | 0.75% | 0.25% | 2% | 96% | 1% | 25% | 5% | 70% |
| OGTE5 | 1% | 0% | 2% | 96% | 1% | 25% | 5% | 70% |

Figure 16

Composition of LCM-based groups for OPPI vs. no OPPI analysis

| | Resin Composition | | | | | Total Composition | | |
|---|---|---|---|---|---|---|---|---|
| | CQ | PPD | DMAEMA | LCM | OPPI | Resin | TS-530 Filler | Treated Foundation Filler |
| LCM1 | 0% | 1% | 2% | 97% | 0% | 25% | 5% | 70% |
| LCM3 | 0.50% | 0.50% | 2% | 97% | 0% | 25% | 5% | 70% |
| LCM5 | 1% | 0% | 2% | 97% | 0% | 25% | 5% | 70% |
| OLCM1 | 0% | 1% | 2% | 96% | 1% | 25% | 5% | 70% |
| OLCM3 | 0.50% | 0.50% | 2% | 96% | 1% | 25% | 5% | 70% |
| OLCM5 | 1% | 0% | 2% | 96% | 1% | 25% | 5% | 70% |

Figure 17

Composition of LCM groups for OPPI self-sufficiency experiment

| | Resin Composition | | | | Total Composition | | |
|---|---|---|---|---|---|---|---|
| | CQ | DMAEMA | LCM | OPPI | Resin | TS-530 Filler | Treated Foundation Filler |
| LCM 5 (CA) | 1% | 2% | 97% | 0% | 25% | 5% | 70% |
| LCM 6 (CO) | 1% | 0% | 97% | 2% | 25% | 5% | 70% |
| LCM 7 (COA) | 1% | 1% | 97% | 1% | 25% | 5% | 70% |

*Note* that LCM 5 and its results are the same as those from the OPPI vs. no OPPI part of the experiment.

Figure 18

DC of GTE samples

| | Cure Time (s) | | | | | | |
|---|---|---|---|---|---|---|---|
| | 0 | 10 | 20 | 40 | 80 | 120 | 240 |
| GTE 1-1 | 0.00% | 38.99% | 49.62% | 53.12% | 56.11% | 56.09% | 59.09% |
| GTE 1-2 | 0.00% | 41.82% | 46.65% | 53.98% | 53.73% | 57.13% | 58.11% |
| GTE 1-3 | 0.00% | 36.46% | 47.26% | 51.63% | 52.74% | 55.45% | 57.59% |
| GTE 2-1 | 0.00% | 40.65% | 49.81% | 53.88% | 57.04% | 57.86% | 60.36% |
| GTE 2-2 | 0.00% | 38.66% | 47.94% | 52.97% | 56.32% | 58.88% | 60.50% |
| GTE 2-3 | 0.00% | 38.66% | 48.78% | 53.18% | 56.65% | 59.03% | 59.74% |
| GTE 3-1 | 0.00% | 40.93% | 50.07% | 55.60% | 58.03% | 55.32% | 57.59% |
| GTE 3-2 | 0.00% | 42.73% | 51.76% | 54.61% | 60.29% | 57.95% | 60.07% |
| GTE 3-3 | 0.00% | 40.86% | 47.45% | 52.50% | 56.38% | 59.81% | 59.81% |
| GTE 4-1 | 0.00% | 44.54% | 52.01% | 56.66% | 60.33% | 61.80% | 61.84% |
| GTE 4-2 | 0.00% | 37.29% | 48.91% | 52.73% | 57.22% | 57.07% | 59.11% |
| GTE 4-3 | 0.00% | 42.06% | 49.62% | 54.95% | 56.43% | 59.34% | 59.90% |
| GTE 5-1 | 0.00% | 46.38% | 50.89% | 54.21% | 57.17% | 54.51% | 55.82% |
| GTE 5-2 | 0.00% | 42.50% | 52.17% | 53.85% | 58.85% | 56.21% | 58.64% |
| GTE 5-3 | 0.00% | 39.16% | 49.20% | 50.55% | 55.56% | 52.97% | 53.95% |

DC of OGTE samples

| | \multicolumn{7}{c}{Cure Time (s)} | | | | | | |
|---|---|---|---|---|---|---|---|
| | 0 | 10 | 20 | 40 | 80 | 120 | 240 |
| ■ | 0.00% | 48.70% | 57.88% | 56.92% | | | |
| OGTE 1-2 | 0.00% | 57.64% | 58.24% | 61.34% | 59.27% | 65.27% | |
| OGTE 1-3 | 0.00% | 54.73% | 55.75% | 61.70% | 61.06% | 63.52% | |
| OGTE 2-1 | 0.00% | 55.98% | 59.55% | 62.30% | 65.05% | 64.99% | 66.65% |
| OGTE 2-2 | 0.00% | 54.23% | 59.83% | 62.24% | 64.15% | 67.12% | 68.36% |
| OGTE 2-3 | 0.00% | 52.52% | 54.28% | 61.22% | 62.05% | 63.54% | 64.89% |
| OGTE 3-1 | 0.00% | 53.01% | 60.09% | | 65.60% | | 65.60% |
| OGTE 3-2 | 0.00% | 54.70% | 58.18% | 55.69% | 59.96% | 61.94% | 58.63% |
| ■ | 0.00% | 55.71% | 59.34% | 64.40% | | | |
| OGTE 4-1 | 0.00% | 59.16% | 58.47% | 64.41% | 65.14% | 65.99% | 67.12% |
| OGTE 4-2 | 0.00% | 54.89% | 59.13% | 60.76% | 63.30% | 63.72% | 64.14% |
| OGTE 4-3 | 0.00% | 53.84% | 58.67% | 60.44% | 63.27% | 63.45% | 63.88% |
| OGTE 5-1 | 0.00% | 56.27% | 57.34% | 58.19% | 64.98% | 66.05% | 66.05% |
| OGTE 5-2 | 0.00% | 53.71% | 56.05% | 58.41% | 57.52% | 55.77% | 62.34% |
| ■ | 0.00% | 51.61% | 58.68% | 58.90% | | | |

Peak deformation at the aliphatic C=C peak.

Figure 21

DC of LCM samples

| | Cure Time (s) | | | | | | |
|---|---|---|---|---|---|---|---|
| | 0 | 10 | 20 | 40 | 80 | 120 | 240 |
| LCM 1-1 | 0.00% | 16.75% | 27.76% | 27.50% | 34.33% | 38.86% | 36.00% |
| LCM 1-2 | 0.00% | 14.61% | 19.31% | 33.82% | 21.47% | 20.33% | 33.25% |
| LCM 1-3 | 0.00% | 24.07% | 32.75% | 38.29% | 41.60% | 41.52% | 47.15% |
| LCM 3-1 | 0.00% | 14.88% | 24.03% | 29.93% | 35.39% | 37.89% | 40.63% |
| LCM 3-2 | 0.00% | 8.62% | 19.16% | 25.49% | 28.89% | 25.73% | 36.11% |
| LCM 3-3 | 0.00% | 18.90% | 27.78% | 35.84% | 39.03% | 41.35% | 44.16% |
| LCM 5-1 | 0.00% | 22.90% | 30.26% | 37.99% | 40.75% | 44.92% | 47.78% |
| LCM 5-2 | 0.00% | 15.57% | 19.02% | 32.64% | 32.91% | 38.22% | 41.62% |
| LCM 5-3 | 0.00% | 7.17% | 18.59% | 30.65% | 35.90% | 36.71% | 40.43% |

Figure 22

DC of OLCM samples

| | Cure Time (s) | | | | | | |
|---|---|---|---|---|---|---|---|
| | 0 | 10 | 20 | 40 | 80 | 120 | 240 |
| OLCM 1-1 | 0.00% | 37.92% | 46.25% | 52.91% | 49.06% | 51.88% | 54.77% |
| OLCM 1-2 | 0.00% | 31.10% | 40.30% | 44.58% | 46.49% | 49.07% | 52.22% |
| OLCM 1-3 | 0.00% | 28.12% | 38.36% | 41.99% | 46.82% | 48.79% | 52.65% |
| OLCM 3-1 | 0.00% | 40.65% | 47.33% | 50.07% | 50.95% | 51.66% | 54.45% |
| OLCM 3-2 | 0.00% | 47.75% | 53.06% | 58.37% | 55.60% | 54.60% | 59.94% |
| OLCM 3-3 | 0.00% | 34.34% | 39.47% | 48.79% | 49.65% | 50.44% | 51.51% |
| OLCM 5-1 | 0.00% | 45.99% | 49.74% | 51.94% | 53.29% | 55.60% | 56.91% |
| OLCM 5-2 | 0.00% | 39.25% | 48.46% | 49.11% | 55.01% | 57.35% | 57.35% |
| OLCM 5-3 | 0.00% | 51.95% | 51.89% | 54.59% | 56.85% | 56.90% | 59.33% |

Line graph comparing the average DC at each curing time for GTE, OGTE, LCM, OLCM samples Graph showing initial conversion rate (calculated for the first 10 seconds of cure)

DC of LCM samples for part 2 of DC analysis

|  | Cure Time (s) | | | | | | |
|---|---|---|---|---|---|---|---|
|  | 0 | 10 | 20 | 40 | 80 | 120 | 240 |
| LCM 5-1 (CA) | 0.00% | 22.90% | 30.26% | 37.99% | 40.75% | 44.92% | 47.78% |
| LCM 5-2 (CA) | 0.00% | 15.57% | 19.02% | 32.64% | 32.91% | 38.22% | 41.62% |
| LCM 5-3 (CA) | 0.00% | 7.17% | 18.59% | 30.65% | 35.90% | 36.71% | 40.43% |
| LCM 6-1 (CO) | 0.00% | 8.96% | 21.33% | 32.58% | 35.68% | 37.72% | 47.25% |
| LCM 6-2 (CO) | 0.00% | 9.89% | 22.67% | 32.92% | 38.82% | 44.22% | 48.38% |
| LCM 6-3 (CO) | 0.00% | 3.64% | 15.10% | 27.74% | 35.52% | 40.75% | 44.90% |
| LCM 7-1 (COA) | 0.00% | 24.06% | 34.47% | 42.77% | 47.05% | 49.29% | 51.71% |
| LCM 7-2 (COA) | 0.00% | 30.85% | 33.60% | 44.58% | 48.55% | 50.73% | 53.47% |
| LCM 7-3 (COA) | 0.00% | 27.73% | 31.43% | 43.92% | 47.90% | 50.96% | 54.26% |

Line graph comparing average cure rates of LCM 5, 6, and 7

Initial conversion rate of LCM 5, 6, and 7 calculated from the first ten seconds of cure.

Shrinkage analysis on the Acuvol

|  | Trial 1 | Trial 2 | Trial 3 | Mean |
|---|---|---|---|---|
| LCM1 | 0.77% | 0.81% | 0.67% | 0.75% |
| LCM3 | 0.84% | 0.86% | 0.58% | 0.76% |
| LCM5 | 0.70% | 0.72% | 0.42% | 0.61% |
| OLCM1 | 0.94% | 1.07% | 0.39% | 0.80% |
| OLCM3 | 0.51% | 0.86% | 1.10% | 0.82% |
| OLCM5 | 0.75% | 0.64% | 1.11% | 0.83% |

Shrinkage averages - LCM vs. OLCM samples

|  | mean |
|---|---|
| LCM | 0.71% |
| OLCM | 0.82% |

# DUAL-CURE DENTAL RESINS AND ADHESIVES WITH INCREASED CURE AND COLOR STABILITY AND LOW COLOR

RELATED APPLICATION

This application claims priority to U.S. provisional patent application No. 60/991,195, titled "Dual-Cure Dental Resins and Adhesives with Increased Cure and Color-Stability, and Low Color," and filed Nov. 29, 2007.

GRANT INFORMATION

This invention was made in part with government support under Grant Nos. T32 DE014318-06 and P01 DE011688, both from NIH/NIDCR.

SUMMARY OF THE INVENTION

In general, various embodiments of the present invention are directed to novel compositions and related methods of manufacture and use for polyacrylate materials and/or light- and/or dual-cure resins that not only have low color, but also are color stable. Various embodiments also have increased degree of cure. Finally, the lower color and color stability allow the use of dual-cure resins in esthetic situations to benefit from the reduced shrinkage stress, an inherent benefit of dual-cure resins. Such polyacrylate materials may be particularly useful in dentistry, orthopedics, other biomedical applications, and/or the like. In an embodiment, the composition comprises a cationic initiator, an electron donor, an ethylenically unsaturated monomer, and/or a photoinitiator.

An important characteristic of current resin systems and the aging of current resin systems is color. Much study and development has been devoted to producing a resin and/or resin system that has no color after curing. However, the art field has been plagued with many problems. Typically, self-cure, light-cure and dual-cure systems with significant amounts of aromatic amines produce a yellow resin that continues to further yellow over time. Light-cured systems are typically less yellow, and have provided improved color stability. Thus, photocurable resins have almost completely replaced two-part self-cure resins as dental restoratives. However, with the development of tooth bleaching techniques, color and color stability (resins yellowing over time) are becoming growing concerns with the rapidly increasing demand for a high level of esthetic quality in dental restorations.

Typically, self-cured and dual-cured resins are used predominantly as cements or luting resins where esthetics is not a primary concern because of the high degree of yellowness in the initial color and the large amount of color shift over time. In the case of bonding porcelain veneers and restorations, where the porcelain is translucent and the color of the luting resin is transmitted through, this yellowness is a problem since typical light-cured resins are not preferable due to the diminished capacity to transmit enough light to completely cure the light-cured resin. This high initial color and color shift is mainly due to the initiating system used in the resins. Redox catalyst systems consisting of a hydroperoxide oxidizing agent and substituted thiourea reducing agent have been used in the past to enhance color-stability of self-cured systems and/or the shelf life of dental resins such as those disclosed in U.S. Pat. No. 3,991,008. However, such self-cured systems have typically low degrees of cure, and, while they are more color-stable than other self-cured systems, they are typically not as color stable as current light-cured systems.

For light-cured systems, since blue light is used for curing, a photoinitiation system that absorbs blue light is required. Thus, the initiator is inherently yellow (the complementary color of blue). Color instability (color changing & darkening over time) often results mainly from oxidation of various resin components such as inhibitors, amine initiators and unreacted polymerizable groups (double bonds). Thus, including onium-ion, or other cationic photoinitiators, and related compounds in the photoinitiation system improves physical properties by increasing monomer conversion (degree of cure), reduces initial color and reduces components that contribute to oxidative color changes. It also contributes to biocompatibility by reducing leachable components such as unreacted monomer, photosensitizers (such as camphorquinone (CQ)), and amine initiators. Published literature reports cytotoxic effects of p-octyloxy phenyl-phenyl iodonium hexafuoantimonate (OPPI) to be in the same range as current photoinitiated resin components, so these compounds are not themselves expected to pose biocompatibility issues.

As such, it was found that in current visible-light photoinitiating systems, the presence of the onium ion compound OPPI increases the efficiency of initiation sufficiently that the typical combination of blue-light-absorbing photosensitzer CQ and proton-donating amine initiator can be substantially reduced while simultaneously increasing both the rate and degree of cure. OPPI is colorless while CQ is yellow. Thus there is a reduction in yellowness and an overall improvement of initial color. In addition, an improvement in color stability under accelerated aging is also attained. Applicants propose that such color stability is due to the reduced amine level, but Applicants do not wish to be bound by such theory.

Furthermore, there are several deficiencies associated with the use of light-cured resins despite its "on demand" curing ability and relatively better color stability as compared to self-cured or dual-cured resins. The first problem is shrinkage stress. Shrinkage stress is a problem with light-cured resins because the rapid curing process, especially with high intensity lamps, causes buildup of tremendous amounts of internal stress, and consequent failure at the bonded interfaces, within the resin or even in the tooth. In addition, about 70% of restorative resins are done to replace previous restorations due to issues that have much to do with incomplete cure, such as the use of lamps with degraded intensity and user error such as short light exposure times, incorrect exposure distance and angle, and difficulty in curing areas where accessibility to light is poor or impossible. One consequence of uncured resin is the leaching of unconverted monomers that can lead to pulpal inflammation. Finally, typical light-cured resins are placed in thin layers to combat the above-mentioned problems, but this is very time-consuming in the clinic and gives rise to increased cost for both dentist and patient.

Typical redox catalyst self-cure systems have lower initial color but also have tremendous color shift. Dual-cure systems using a conventional light-cure initiator system with this low-color self-cure system produce comparable or lower initial color relative to light-cure systems, but all have significantly larger color shifts and often have decreased degree of cure and mechanical properties. Thus, a dual-cure system that contains a redox catalyst self-cure initiator system and an onium photoinitiator, or other cationic photoinitiators, that are also low-color and color-stable would provide enhanced characteristics. Such a system could be cured such that a significant portion of the cure occurs slowly, allowing stress relaxation and reducing stress buildup, while at the same time potentially producing resins with a higher degree of cure and therefore better mechanical properties. This system would also allow for curing in thicker layers, in various embodiments, saving either or both time and expense.

U.S. Pat. No. 6,982,288 claims the use of ionic redox polymerization and at least one secondary ionic salt for enhanced shelf life before cure. In that patent, systems using the redox catalyst systems consisting of a hydroperoxide oxidizing agent and a substituted thiourea reducing agent, and the possibility of having a photoinitiator are described in the claims.

U.S. Pat. No. 7,173,074 claims the use of polymerizable urea or thiourea compounds that function as reductants. However, the patent focuses on water-based dental cements that contain an acid-functional component.

Surprisingly, the data presented below indicates that the addition of a general photoinitiator system to the color-stable self-cure system does not automatically result in a color-stable dual-cure system. In fact, the data presented herein illustrates that a system without an onium photoinitiator has more color and is less color-stable than light-cured systems. Also, counterintuitively, in the optimal combinations with the lowest color shift, the addition of the onium photoinitiator into the dual-cure system has not reduced the concentrations of the typical blue-light-absorbing photosensitzer CQ and proton-donating amine initiator. Thus, there is a synergistic reaction that is taking place and when the onium photoinitiator is added.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE FIGURES

The forgoing summary as well as the following detailed description of the preferred embodiment of the invention will be better understood when read in conjunction with the appended drawings. It should be understood, however, that the invention is not limited to the precise descriptions and instrumentalities shown herein, with emphasis instead being placed upon clearly illustrating the principles of the present invention. For a more complete understanding of the present invention, and the advantages thereof, reference is now made to the following descriptions taken in conjunction with the accompanying drawings, in which:

FIG. 1 illustrates the experimental groups for degree and rate of conversion of light-cured resins FIG. 2 illustrates the degree of conversion (DC, %) of a blend of BisGMA, TEGDMA, and BisEMA (GTE) with various photoinitiators.

FIG. 5 illustrates the color coordinates.

FIG. 6 illustrates the color change ($\Delta E$)—Mean (S.D.).

FIG. 15 illustrates the composition of GTE-based groups for OPPI vs. no OPPI analysis.

FIG. 16 illustrates the composition of liquid crystal monomer (LCM)-based groups for OPPI vs. no OPPI analysis.

FIG. 17 illustrates the composition of LCM groups for OPPI self-sufficiency experiment.

FIG. 18 illustrates the DC of GTE samples.

FIG. 21 illustrates the DC of LCM samples.

FIG. 22 illustrates the DC of OLCM (LCM with OPPI added to the initiator system) samples.

DETAILED DESCRIPTION

Figure 3:
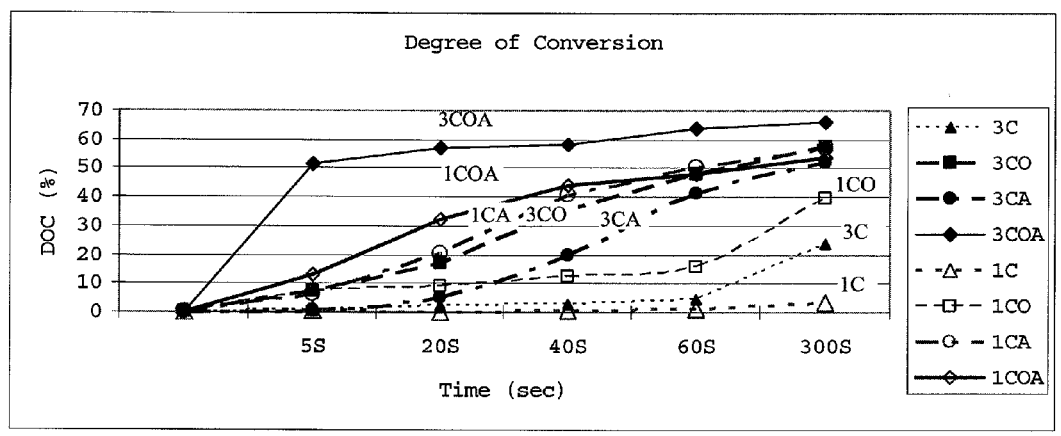
FIG. 3 illustrates the DC of GTE with various photoinitiators vs. exposure time.

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

The following definitions and explanations are meant and intended to be controlling in any future construction unless clearly and unambiguously modified in the following Description or when application of the meaning renders any construction meaningless or essentially meaningless. In cases where the construction of the term would render it meaningless or essentially meaningless, the definition should be taken from Webster's Dictionary, 3rd Edition. Definitions and/or interpretations should not be incorporated from other patent applications, patents, or publications, related or not, unless specifically stated in this specification or if the incorporation is necessary for maintaining validity.

As used herein, the term "patient" means and refers to a human or animal.

As used herein, the term "chemically feasible" refers to a connectivity of atoms such that the chemical valency of each atom is satisfied. For example, an oxygen atom with two bonds and a carbon atom with four bonds are chemically feasible.

As used herein, the term "dual-cure" means and refers to a system that cures at least partially by light-cure (electromagnetic radiation) and at least partially by self-cure.

As used herein, the term "self-cure" means and refers to a system that cures over time and/or without substantial external stimulus.

As used herein, the term "water soluble" or use of the term "miscible in water" means and refers to a level of solubility such that when a composition is placed in water, greater than about 2.0 percent by weight of the composition dissolves. For example, methyl methacrylate (MMA) is considered substantially non water soluble, yet has a water solubility of 1.6 g in 100 g of water.

Other than in the operating examples, or where otherwise indicated, all numbers expressing quantities of components used herein are to be understood as modified in all instances by the term "about".

In developing embodiments of the present invention, it was found that the addition of an onium photoinitiator, or other cationic polymerizer, to a light-cured system lowered initial color and produced better color stability and higher degree of conversion than the standard commercial light-cured systems. Surprisingly, the combination of onium-organic compounds with a photosensitizing compound and/or other photo-initiating combinations of compounds, also initiated free-radical polymerization in acrylic resins such as those used in dentistry, orthopedics, biomedical applications, coatings and/or the like.

As such, various embodiments of a light-cured embodiment of the present invention comprise a composition comprising an onium ion compound (which is a cationic initiator/polymerizer), a photoinitiator, an amine (having strong proton-donating capacity) and, optionally, a combination of one or more oligomers, monomers, and/or polymers. In further embodiments, various embodiments of the present invention comprise compositions comprising a diaryliodonium hexaflueorantimonate, an α-diketone initiator, an acrylated tertiary amine, and one or more acrylate and/or methacrylate monomers. In an embodiment, a composition of the present invention comprises a p-octyloxyphenyl phenyl iodonium hexafluoroantimonate (OPPI), camphorquinone (CQ), 2-dimenthylaminoethyl methacrylate (DMAEMA), and at least one monomer, at least one polymer, and/or at least one oligomer. OPPI is a diaryliodonium hexafluoroantimonate.

Suitable visible light-induced and ultraviolet light-induced initiators will be familiar to those skilled in the art. In various embodiments, visible light-induced initiators include camphorquinone, diaryliodonium simple or metal complex salts, chromophore-substituted halomethyl-s-triazines and halomethyl oxadiazoles. In other embodiments, visible light-induced photoinitiators include combinations of an alpha-diketone such as camphorquinone, and a diaryliodonium salt such as diphenyliodonium chloride, bromide, iodide or hexafluorophosphate. In alternate embodiments, ultraviolet light-induced polymerization initiators include amines that are optionally polymerizable.

Various embodiments of the present invention comprise methods of forming a hardened composition from a self-cured component and a light-cured component, from at least two portions, said method comprising the steps of: a first portion comprising a polymerizable reducing agent and a light-cured portion comprising a resin system, a photoinitiator, and an amine co-initiator, and a second portion comprising an oxidizing agent, whereby the polymerizable reducing agent and the oxidizing agent comprise a self-cured component; and, contacting said first portion and said second portion, wherein a hardened composition is formed.

In an alternate embodiment, the first portion comprises the oxidizing agent and the second portion comprises the polymerizable reducing agent.

In an alternate embodiment, in a dual-cured system, the first portion and the second portion comprise, in any combination, a self-cured component comprising a polymerizable reducing agent and an oxidizing agent and a light-cured component comprising a resin system, a photoinitiator, and an amine co-initiator, wherein said polymerizable reducing agent and oxidizing agent are not present in the same portion. Makeup of the first portion and the second portion can vary as desired as long as the polymerizable reducing agent and the oxidizing agent are not in the same portion.

In addition, the combination of an onium photoinitiator, or other cationic polymerizer, component (light-cure portion) and redox polymerization component (self-cure portion) in a dual-cure resin system, lowered initial color and produced better color stability than the standard commercial light, self or dual-cured systems, and increased degree of conversion. The system also had significantly better color stability and degree of cure than redox catalyst self-cure systems consisting of hydroperoxide oxidizing agent and a substituted thiourea reducing agent, and lower initial color and enhanced color stability as compared to dual-cure systems using redox catalyst self-cure systems consisting of hydroperoxide oxidizing agent and a substituted thiourea reducing agent and standard commercial photoinitiator systems such as CQ and DMAEMA, illustrating a synergistic effect. It is counterintuitive that this, at least one of lower initial color, color stability, and enhanced degree of cure, was achieved without necessarily reducing the concentrations of the commercial photoinitiator system such as CQ and DMAEMA. This is clearly a synergistic relationship as is further demonstrated by the fact that there are no clear trends to be identified in the dual-cure combinations.

Illustrative amine co-initiators include tertiary amines. Suitable tertiary amines comprise ethyl 4-(N,N-dimethylamino)benzoate, N,N-dimethylaminoethyl methacrylate (DMAEMA), diethylaminoethyl methacrylate (DEAEMA), ethyl 4-dimethylaminobenzoate, dimethyl-p-toluidine, dihydroxyethyl-p-toluidine, N,N-cyanoethyl-methylaniline (CEMA), and and the like. However, generally, any co-initiator can be used, such as any proton-donating alkyl or aromatic amines The initiator can be employed in catalytically-effective amounts, such as from about 0.1 to about 5 weight percent, based on the weight of ethylenically-unsaturated compound present. In various other embodiments, the amine co-initiator comprises about 5.0 percent by weight of the total weight of the hardenable composition. In an alternate embodiment, the amine co-initiator comprises about 3.0 percent by weight of the total weight of the hardenable composition. In an alternate embodiment, the amine co-initiator comprises about 1.0 percent by weight of the total weight of the hardenable composition. In an alternate embodiment, the amine co-initiator comprises at least 0.1 percent by weight of the total weight of the hardenable composition. In an alternate embodiment, the amine co-initiator comprises at least 5.0 percent by weight of the total weight of the hardenable composition.

In various embodiments, herein disclosed are light-cure and dual-cure resins that exhibit one or more of reduced color, increased color stability, and/or increased degree of cure. In various embodiments, such improvements were obtained by using a combination of an onium photoinitiator, or other cationic polymerizer, such as tris(methylphenyl) sulfonium hexafluoroantimonate, 4-decyloxyphenyl) phenyliodonium hexafluoroantimonate, diphenyliodonium hexafluoroantimonate (DP), [4(1-octadecylphenoxyacetate)]phenyl iodonium hexafluoroantimonate (OPPA) or (4-octadecyloxyphenyl)phenyl iodonium hexafluoro hexafluoroantimonate (OPP), an amine component for the light-cured resin portion and a non-amine-containing redox polymerization system for the self-cured portion or component. Such combination was more than a simple matter of adding two components to optimally combine two functions, as our results show that combining a standard commercial light-cure with the redox self-cure system developed color, or yellow, upon curing and/or over time as compared to light-cure systems, and the reduction in the commercial light-cure initiators is not necessary in the optimal, most color-stable combinations.

In various embodiments, the self-cure portion or component of dual-cure compositions of the present invention include a light-cure component, a resin system, a polymerizable reducing agent comprising at least one of either urea group(s), thiourea group(s), their derivatives, and/or other reducing components as are common in the art, and an oxidizing agent. In an embodiment, the compositions comprise a secondary reducing agent that can be either polymerizable or non-polymerizable. In various embodiments, the reducing agents and/or oxidizing agents are selected such that they are miscible in the respective composition, but in no embodiment is the composition miscible in water.

For a dual-cure system, the reducing and oxidizing agents are discussed together. They should react with or otherwise cooperate with one another to produce free-radicals capable of initiating polymerization of the resin system. This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system, but are not water soluble or miscible in water to permit ready dissolution in the other components of the hardenable composition.

The reducing agents of the present invention optimally include a polymerizable reducing agent and optionally a secondary reducing agent, which may or may not be polymerizable. These reducing agents can be in the form of a monomer, oligomer, or polymer. Urea and thiourea groups are known to function as reductants in oxidation-reduction (i.e., redox) polymerization reactions. In addition, derivatives of urea and thiourea are also useful as polymerizable reducing agents. Various combinations of such polymerizable reducing agents can be used if desired. Urea compounds include, for example, derivatives of barbituric acid such as 5-acryloxyalkyl barbituric acid, 5-allyl 5-isopropyl barbituric acid, and 5-ethyl 5-crotyl barbituric acid.

In various further embodiments, a secondary reducing agent is used. Secondary reducing agents can be either polymerizable or nonpolymerizable. Embodiments of secondary reducing agents include ascorbic acid, ascorbic acid derivatives, and metal complexed ascorbic acid compounds; amines; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; cobalt (II) chloride, ferrous chloride, ferrous sulfate, hydrazine, hydroxylamine, oxalic acid, salts of a dithionite or sulfite anion, and mixtures thereof.

Typically, with the use of the polymerizable urea or thiourea reducing agent and the secondary reducing agent, significant advantages can be realized. This combination provides a balance of properties with respect to color stability of both the hardenable and hardened compositions, toxicity of the hardened composition, and reaction time ("snap set") of the hardenable composition, along with the shelf stability of the components of the hardenable composition.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, sodium peroxide, hydrogen peroxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

The reducing and oxidizing agents are present in an amount sufficient to permit an adequate free-radical reaction rate. This can be evaluated by combining all of the ingredients of the hardenable composition except for the optional filler, and observing whether or not a hardened mass is obtained.

In various embodiments, the polymerizable reducing agent is present in an amount of at least about 0.01 wt-% based on the total weight of the components of the hardenable composition. In an alternate embodiment, the polymerizable reducing agent is present in an amount of at least about 0.1 wt-% based on the total weight of the components of the hardenable composition. In various embodiments, the polymerizable reducing agent is present in an amount of no greater than about 50 wt-% based on the total weight of the components of the hardenable composition. In an alternate embodiment, the polymerizable reducing agent is present in an amount of no greater than about 40 wt-% based on the total weight of the components of the hardenable composition. In an alternate embodiment, the polymerizable reducing agent is present in an amount of no greater than about 30 wt-% based on the total weight of the components of the hardenable composition In an alternate embodiment, the polymerizable reducing agent is present in an amount of no greater than about 20 wt-% based on the total weight of the components of the hardenable composition. In an alternate embodiment, the polymerizable reducing agent is present in an amount of no greater than about 15 wt-% based on the total weight of the components of the hardenable composition. In an alternate embodiment, the polymerizable reducing agent is present in an amount of no greater than about 10 wt-% based on the total weight of the components of the hardenable composition. In an alternate embodiment, the polymerizable reducing agent is present in an amount of no greater than about 5.0 wt-% based on the total weight of the components of the hardenable composition.

In various embodiments, the oxidizing agent is present in an amount of at least about 0.01 wt-% based on the total weight of the components of the hardenable composition. In an alternate embodiment, the oxidizing agent is present in an amount of at least about 0.1 wt-% based on the total weight of the components of the hardenable composition. In an embodiment, the oxidizing agent is present in an amount of no greater than about 50 wt-% based on the total weight of the components of the hardenable composition. In an alternate embodiment, the oxidizing agent is present in an amount of no greater than about 40 wt-% based on the total weight of the components of the hardenable composition. In an alternate embodiment, the oxidizing agent is present in an amount of no greater than about 30 wt-% based on the total weight of the components of the hardenable composition. In an alternate embodiment, the oxidizing agent is present in an amount of no greater than about 20 wt-% based on the total weight of the components of the hardenable composition. In an alternate embodiment, the oxidizing agent is present in an amount of no greater than about 10 wt-% based on the total weight of the components of the hardenable composition. In an alternate embodiment, the oxidizing agent is present in an amount of no greater than about 5.0 wt-% based on the total weight of the components of the hardenable composition.

As is common in the art, the reducing or oxidizing agents can be microencapsulated which is commonly thought to enhance shelf stability of the hardenable composition, and if necessary permit packaging the reducing and oxidizing agents together.

In an embodiment, at least one monomer is a mixture of monomers. In an alternate embodiment, the polymer is a mixture of polymers. In an alternate embodiment, the oligomer is a mixture of oligomers. In yet an alternate embodiment, the composition comprises a mixture of one or more monomers and/or one or more polymers and/or one or more oligomers. In general, any cationic initiator and any electron donor with a labile proton can be used. Surprisingly, these compositions have a higher degree of cure, color stability and/or lower color than conventional light-cured systems. In various embodiments, OPPI increases degree of cure (DC).

In various embodiments of a composition of the present invention comprises a resin system comprising one or more ethylenically unsaturated monomers, oligomers, polymers, and/or the like. Further, in various embodiments, the polymerizable reducing agent is capable of also being a polymerizable monomer, oligomer, polymer, and/or the like.

The components of the resin system are at least sufficiently miscible that they do not undergo substantial phase separation when combined with the other ingredients/components of the composition. As herein described, components of the resin system are capable of including monomers, oligomers, polymers, combinations thereof, and/or the like.

The resin systems of the hardenable compositions of the present invention typically include an ethylenically unsaturated component. In various embodiments, the ethylenically unsaturated component includes components that can provide altered properties such as toughness, adhesion, set time, and the like. In various embodiments such components comprise suitable alpha-diketones such as 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

For hardening cationically curable resins, cationic polymerizers, examples of useful aromatic iodonium complex salts (such as is used as a component of a ternary photoinitiator system) comprise diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate (DPISbF$_6$).

Of the aromatic iodonium complex salts which are suitable for use in the compositions of the invention diaryliodoniun hexafluorophosphate and diaryliodonium hexafluoroantimonate are among various embodiments. These salts are used because, in general, they promote faster reaction, and are more soluble in suitable ethylenically unsaturated compounds and in inert organic solvents than are other aromatic iodonium salts of complex ions. Suitable ethylenically unsaturated compounds are also available from a wide variety of commercial sources.

Various embodiments comprise a sufficient quantity of ethylenically unsaturated component to provide the desired setting or hardening rate and desired overall properties following hardening. In an embodiment, the mixed but unset hardenable compositions of the invention contain at least about 1.0 percent by weight (wt-%) of an ethylenically unsaturated component, based on the total weight of the hardenable (mixed but substantially unset) composition. In an alternative embodiment, the mixed but unset hardenable compositions of the invention contain at least about 5.0 percent by weight (wt-%) of an ethylenically unsaturated component, based on the total weight of the hardenable (mixed but substantially unset) composition. In an alternative embodiment, the mixed but unset hardenable compositions of the invention contain at least about 10 percent by weight (wt-%) of an ethylenically unsaturated component, based on the total weight of the hardenable (mixed but substantially unset) composition. In an alternative embodiment, the mixed but unset hardenable compositions of the invention contain at least about 25 percent by weight (wt-%) of an ethylenically unsaturated component, based on the total weight of the hardenable (mixed but substantially unset) composition. In general, in various embodiments, the mixed but unset hardenable compositions of the invention contain any chemically feasible amount of an ethylenically unsaturated component.

In various embodiments, the mixed but unset hardenable compositions of embodiments of the present invention contain from about 0.01% to about 95% of an ethylenically unsaturated component, based on the total weight of the hardenable (mixed but unset) composition. In an alternative embodiment, the mixed but unset hardenable compositions of embodiments of the present invention contain from about 0.1% to about 75% of an ethylenically unsaturated component. In an alternative embodiment, the mixed but unset hardenable compositions of embodiments of the present invention contain from about 0.50% to about 50% of an ethylenically unsaturated component. In an alternative embodiment, the mixed but unset hardenable compositions of embodiments of the present invention contain from about 1.0% to about 25% of an ethylenically unsaturated component. In general, in various embodiments, the mixed but unset hardenable compositions of embodiments of the present invention contains any chemically feasible percentage of an ethylenically unsaturated component.

Various compositions of the present invention can be used in a variety of applications, including, but not limited to medical, dental applications, coatings, and other resin based applications for construction and the like. When used in dental applications, such as dental adhesives, dental cements, and dental composites, the hardenable (typically, curable) composition may bond directly to dental enamel, dentin, directly to the gum or other tissue, and/or the like as is common in the art. Embodiments of these systems could be used with esthetic restorations, adhesives, resin cement luting agents, and a variety of resin materials throughout dental practice, biomedical practice, coatings practice and/or the like. The broad application of dental resins and composites comprise, but are not limited to, as would be understood by one of ordinary skill in the art, tooth-colored fillings, luting resins, esthetic veneering, cavity base and liners, provisional restorations, fixed partial dentures, and/or the like. Alternatively, a primer layer can be used on the dental enamel and/or dentin on which the hardenable composition is used.

Both the light-cured and the dual-cured compositions of the invention are particularly well adapted for use as a wide variety of dental materials, which may be filled or unfilled. Although the presence of fillers and pigments can help mask the color and color shift somewhat, it is anticipated that various embodiments of the present invention will produce the same or better results. In further embodiments, compositions of the present invention can be used in sealants or adhesives, which are lightly-filled composites or unfilled compositions that are cured after being disposed adjacent to a tooth (i.e., placing a dental material in temporary or permanent bonding or touching contact with a tooth). The compositions can further be used in composites, which are typically filled compositions. The compositions can further be used in restoratives, which are composites that are polymerized after being disposed adjacent to a tooth. The compositions can further be used in prostheses, which are composites that are shaped and polymerized for final use (e.g., as a crown, bridge, partial denture, veneer, inlay, onlay, or the like), before being disposed adjacent to a tooth. The compositions can further be used in architecture, lithography, coatings and/or the like. Such preformed articles can be ground or otherwise formed into a custom-fitted shape by the dentist or other user.

The components of the hardenable composition can be included in a kit, where the contents of the composition are packaged in component mixtures, as disclosed herein and as understood by one of ordinary skill in the art, to allow for storage and convenient use of the components when they are needed.

When used as a dental composition, the components of the hardenable compositions can be mixed and clinically applied using conventional techniques. In some embodiments, the compositions can provide very good adhesion to dentin, enamel, and/or other tissue, without requiring hard tissue pretreatment. In various embodiments, a primer layer can be used on tissue and/or dental implements on which the hardenable composition is used.

When used as a dental composition, the components of the hardenable compositions can be mixed and clinically applied using conventional techniques. A curing light is not absolutely required (unless a photoinitiator has been included in the composition). The compositions can provide very good adhesion to dentin and/or enamel, without requiring hard tissue pretreatment. Alternatively, a primer layer can be used on the tooth tissue on which the hardenable composition is used.

Preparation and use of the Compositions

The compositions of the present invention are adjusted to provide an appropriate balance of properties in the hardenable composition, both during the setting reaction and after the composition has hardened. These properties include the color stability, the toxicity and the reaction time ("snap set") of the cured composition, along with the shelf stability of the components of the hardenable composition. For example, in embodiments, the hardenable composition should preferably have a snap set of less than or equal to about two (2) minutes for a dental application. The time can vary, but is preferably short so as to maximize the convenience to the patient. The total working time or set time of a composition (i.e., the time for a hardenable resin to cure from a liquid or paste state into a solid material under moisture and temperature conditions similar to those within an oral cavity) is preferably less than about 6 minutes, and more preferably less than about 4 minutes.

The hardenable compositions of the invention can be supplied in a variety of forms including two-part powder/liquid, paste/liquid, and paste/paste systems. Other forms employing multi-part combinations (i.e., combinations of two or more parts), each of which is in the form of a powder, liquid, gel, or paste are also possible. In a multi-part system, one part typically contains the reducing agent(s) and a second part typically contains the oxidizing agent(s).

Fillers

Various embodiments of the present invention further comprise fillers. Fillers may be selected from one or more of a wide variety of materials suitable for incorporation in compositions used for medical or dental applications, such as fillers currently used in dental restorative compositions, and the like. The filler is, in an embodiment, finely divided. The filler can have a unimodal or polymodal (e.g., bimodal) particle size distribution. In an embodiment, the maximum particle size (the largest dimension of a particle, typically, the diameter) of the filler is less than about 10 micrometers, and more preferably less than about 2.0 micrometers. In an embodiment, the average particle size of the filler is less than about 3.0 micrometers, and more preferably less than about 0.6 micrometer.

In various embodiments, the filler can be an inorganic material. In an embodiment, it can also be a cross-linked organic material that is insoluble in the resin system, and is optionally filled with inorganic filler. As should be understood, in most embodiments, the filler should in any event be nontoxic and suitable for use in the mouth. Further, in various embodiments, the filler can be radiopaque or radiolucent and/or fluoride-elutable.

Examples of suitable inorganic fillers include, but are not limited to, naturally occurring or synthetic materials including, but not limited to: quartz; nitrides (e.g., silicon nitride); glasses derived from, for example, Ce, Sb, Sn, Ba, Zn, and Al; feldspar; borosilicate glass; kaolin; talc; titania; low Mohs hardness fillers such as those described in U.S. Pat. No. 4,695,251 (Randklev), herein incorporated by reference; and colloidal and submicron silica particles (e.g., pyrogenic silicas such as those available under the trade designations AEROSIL, including "OX 50", "130", "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like. Preferred non-acid-reactive filler particles are quartz, submicron silica, and non-vitreous micro-particles of the type described in U.S. Pat. No. 4,503,169 (Randklev), herein incorporated by reference. Mixtures of these non-acid-reactive fillers are also contemplated, as well as combination fillers made from organic and inorganic materials.

In various embodiments, glasses include borate glasses, phosphate glasses, and fluoroaluminosilicate ("FAS") glasses. FAS glasses are particularly preferred. The FAS glass preferably contains sufficient elutable cations so that a hardened dental composition will form when the glass is mixed with the components of the hardenable composition. The glass also preferably contains sufficient elutable fluoride ions so that the hardened composition will have cariostatic properties. The glass can be made from a melt containing fluoride, alumina, and other glass-forming ingredients using techniques familiar to those skilled in the FAS glassmaking art.

The amount of filler should be sufficient to provide a hardenable composition having desirable mixing and handling properties before hardening, and good performance after hardening. In various embodiments, a filler comprises between about 0.01% by weight to about 95% by weight. In an alternative embodiment, a filler comprises between about 0.1% by weight to about 75% by weight. In an alternative embodiment, a filler comprises between about 0.5% by weight to about 50% by weight. In an alternative embodiment, a filler comprises between about 1.0% by weight to about 25% by weight. However, the filler is capable of being present in any amount that is chemically feasible.

Optional Additives

Optionally, the hardenable compositions also may contain solvents (e.g., alcohols) or diluents. If desired, the hardenable composition of the invention can contain adjuvants such as pigments, inhibitors, accelerators, viscosity modifiers, surfactants, and other ingredients that will be apparent to those skilled in the art. Embodiments with appropriate comonomers and/or fluoride leachable fillers can also provide long-term fluoride release. Hence the compositions of the invention may provide fluoride release for cariostatic effect.

As such, various embodiments comprise a hardenable composition comprising a light-cured portion component comprising a photoinitiator component comprising a cationic polymerizer, an amine co-initiator, and a resin system, wherein the photoinitiator component is not miscible in water. In all embodiments, the resin system contains no acid functionalized components. In a further embodiment, the hardenable composition comprises a self-cured portion, comprising a polymerizable reducing agent and an oxidizing agent. Further embodiments comprise kits with various components of the hardenable compositions.

Various further embodiments disclose methods of forming a hardened composition from at least two portions, the method comprising: providing a light-cured portion comprising a resin system, a photoinitiator, and an amine co-initiator, and a self-cured portion comprising a polymerizable reducing agent and oxidizing agent, and contacting the light-cured portion and the self-cured portion, whereby a hardened composition is formed. In various embodiments, a step of exposing the light-cured portion and the self-cured portion to a source of electromagnetic radiation is performed.

Various embodiments of the hardenable compositions of the present invention find utility as at least one of a dental adhesive, a dental cement, a dental composite, such as, but not limited to a tooth-colored filling, a luting resin, an esthetic veneer, a cavity base, a liner, a provisional restoration, a fixed partial denture, and/or the like.

Various further embodiments disclose methods for repairing a tooth of a patient, the method comprising the steps of applying the composition as herein disclosed to the tooth.

An alternate embodiment comprises a dual-cured hardenable composition comprising a light-cured portion and a self-cured portion, said light-cured portion comprising a photoinitiator component comprising a cationic polymerizer, an amine co-initiator, and a resin system, wherein said photoinitiator component contains no acid functionalized components and wherein said dual-cured hardenable composition comprises at least one of an enhanced degree of cure, enhanced color stability, and low initial color, as compared to conventional light-cured and dual-cured hardenable composition comprising an acid functionalized component and, in general, other prior art dual-cure, light-cure and self-cure hardenable compositions.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

EXAMPLES

Photopolymerization uses light energy to initiate photochemical and chemical reactions in organic oligomers, to form new polymeric materials by the photo-induced increase of molecular weight by monomer to polymer conversion, as well as crosslinking of developing or preexisting macromolecules. It has been noted that improved photopolymerization is critical for the optimization of mechanical properties, biocompatibility, and color stability of light-activated dental resins.

Free-radical polymerization can be initiated by the excitation of suitable photoinitiating systems (PISs) under electromagnetic radiation, since direct formation of reactive species on the monomer by light absorption is not an efficient way. Most of these systems were originally sensitive to UV light, but now a large number of various systems allow extension of the spectral sensitivity (that corresponds to the best matching between the emission spectrum of the light source and the absorption spectrum of the formulation) to visible light. In addition, the number and reactivity of these primary radicals modulate the early stages of polymerization kinetics, the polymeric chain lengths and even the final degree of conversion.

The visible light photosensitizer camphorquinone (CQ), an alpha dicarbonyl that absorbs blue light at 468 nm, is widely used in dental resin and adhesive formulations. This can produce a pair of free radicals by abstraction of an active proton. Proton abstraction can be efficiently accomplished by the formation of a complex between the photoexcited sensitizer and an electron-donating (reducing) agent such as a tertiary amine. CQ is a solid yellow compound so that large amounts of CQ in resin formulations lead to an undesirable yellow color, affecting the final aesthetic appearance of the cured material. This, in turn, places practical limits on the concentration of CQ and, consequently, limits the degree of polymerization and depth of cure that can be attained. Other photosensitized initiator systems that are cured by light in the blue region of the electromagnetic spectrum will also have a yellow to amber appearance, since yellow is the complementary color of blue.

Therefore, there has been substantial effort to improve this curing system by the use of alternative photo sensitizers and various amine reducing agents. In recent years manufacturers have also included different photoinitiators in the organic matrix to act either alone, additively or synergistically with CQ. For example, the .-diketone PPD (1-phenyl 1,2-propanedione) is used in adhesives and composite resin formulations to improve the polymerization kinetics and lessen photo-yellowing effects [see, for example, Park, Y-J, Rawls H R and Chae K-H. Photosensitizers for free radical polymerization initiation resins, and method of making the same. (U.S. Pat. No. 6,204,302), Mar. 20, 2001.]

In certain of the examples described below, the onium compound p-octyloxy-phenyl-phenyl iodonium hexafluoroantimonate (OPPI) was used as a photoinitiator. It absorbs at 300-380 nm, which is outside the range of visible wavelengths, and is therefore colorless.

Although it has been reported that almost no polymerization occurs when OPPI is used alone, Eick J D et al. (In vitro biocompatibility of oxirane/polyol dental composites with promising physical properties, *Dental materials* 2002; 18(5): 413-21), investigated it as a cationic photoacid initiator in combination with a visible light sensitizer, CQ, and an electron donor, ethyl 4-dimethylaminobenzoate (EDMAB) to polymerize an oxirane/polyol resin. In their study, photocuring was accomplished by the generation of a strong acid released during the fragmentation of the diphenyliodonium salt photoinitiator. The acid protonates the oxirane groups and initiates cationic polymerization.

Thus, some examples are included to show that OPPI can be used as one component of a free-radical photoinitiator system, and can improve color stability in acrylic resins such as those used in dental (e.g., adhesives and restorations) and other biomedical applications. For this, OPPI was evaluated for its effect on the degree and rate of conversion and color stability of photoinitiated BisGMA-based resins.

Example 1

Novel free-radical photoinitiator systems that improve rate and degree of conversion, color and color stability of light curing resins

Issue 1

Investigating p-octyloxy-phenyl-phenyl iodonium hexafuoroantimonate (OPPI) as a photoinitiator, in combination with camphorquinone/amine photoinitiation systems, for use with di(meth)acrylate-based composite resins. The investigation determined if the inclusion of OPPI improved degree and rate of conversion, initial color and color stability of a representative composite resin dental material.

Method

CQ and OPPI were combined in various proportions with the amine co-initiator 2-dimethylaminoethyl methacrylate (DMAEMA) and used at two levels in which CQ+OPPI+DMAEMA=1 wt. % or 3 wt. % to photo-initiate a BisGMA/BisEMA/TEGDMA (37.5:37.5:25 wt. %) monomer blend.

A total of eight groups (4 groups for each level of total photoinitiator, 1% and 3%) were tested according to the following proportion of components in the photoinitiator system:

Group C: CQ only
Group CO: CQ+OPPI (1:2)
Group CA: CQ+DMAEMA (1:2)
Group COA: CQ+OPPI+DMAEMA (1:1:1)

Each monomer was polymerized using a quartz-halogen curing unit (Demetron 400, Demetron Research Corp., Danbury, Conn.)) with an intensity of 400 mW/cm$^2$ for 5 s, 20 s, 40 s, 60 s, 300 s and their conversion levels (DC) were determined at each exposure time using a Fourier transform infrared spectrophotometer (FTIR).

To examine color stability, experimental composite resins were made by mixing 3.2% silanated barium glass (78% wt., average filler size; 1 micron) with each monomer system, except both CQ only groups and 1% CO group, which were found to cure insufficiently to be able to prepare useful specimens. Disk shaped samples (10 mm in diameter and 1.5 mm in thickness) were made and stored under the conditions of dry or saline solution at room temperature (25° C.) or 60° C. water bath.

Each CIELAB scale was determined with a colorimeter (CHROMA METER CR-400) at the time of baseline (day after curing), 1 week, 2 weeks, and 4 weeks later

Results

The high level (3%) photoinitiated groups exhibited greater DC than the low level (1%) groups. In the 3% group, the COA group showed the fastest and the highest DC, while in the 1% group the CA and COA groups showed the greatest DC.

In the color stability test, both CA groups were darker and more yellow than the CO and COA groups. Color was more stable in composite resins containing OPPI than those containing only the CQ and amine components. The least color change (greatest color stability) was found using 25° C. saline solution ageing, and the most change (least color stability) occurred 60° C. dry air ageing.

OPPI can be used to replace the amine in a given CQ/amine photoinitiator system to accelerate cure rate, increase conversion, reduce initial color and increase color stability.

OPPI can also be included with CQ and amine to allow reduction in CQ and amine concentration while maintaining or improving rate and degree of conversion and producing a very low color with improved color stability.

Finally, including OPPI as a co-initiator with CQ and amine provides an increased range of trade-offs among curing and esthetic characteristics.

Example 2

Materials and Methods

Monomer mixture was made by mixing 37.5 wt % BisGMA (lot #568-21-07, ESSTECH, Essington, Pa.), 37.5 wt % BisEMA (lot #474-32-02, ESSCHEM Inc. Linwood, Pa.), and 25 wt % TEGDMA (lot #597-23-02, ESSTECH).

Total concentrations of 1 wt % and 3 wt % of variously proportioned photo-initiators (CQ/OPPI) or/and DMAEMA were added to make the monomer mixture curable. Eight groups (four groups in each concentration) according to the weight proportion of those components were tested (Table 1). Those kinds of works were done under filtered orange light.

1. Degree and Rate of Conversion

FT-IR, HPLC, and NMR have mainly been used for the determination of the photopolymerization efficiency of dental resins. However, the use of FT-IR absorption spectroscopy is the easiest and simplest method. Therefore, degree of conversion (DC) was determined using a Fourier transform infrared (FTIR) spectrophotometer (Nicolet 520, Nicolet Instrument Corp., Madison, Wis.) in this study.

A small amount of uncured resin monomer was placed between two NaCl disks and the spectrum recorded in transmission with 40 scans at a resolution of 1 $cm^{-1}$ (baseline). After the IR spectral scan, the monomer mixture was cured between the transparent NaCl disks for 5, 20, 40, 60, and 300 seconds with a Demetron 400 visible light curing unit (Demetron Research Corp., Danbury, Conn.). The light-intensity of the curing-unit was measured prior to the fabrication of each sample set (about 440 $mW/cm^2$) using a Model 100 Optilux radiometer (Kerr, Dansbury, Conn.).

After each exposure time, the specimens were again scanned for their FTIR spectra. Remaining unconverted double bonds were calculated by comparing the ratio of aliphatic C=C absorption at 1637 or 1638 $cm^{-1}$ to aromatic carbon-carbon absorption at 1608 $cm^{-1}$ between cured and uncured specimens.

Absorption of the aromatic carbon-carbon stretching band remains constant during polymerization and serves as an internal standard where the DC of each specimen was equal to 100% minus (% C=C) equation.

$$\left(1 - \frac{(\text{aliphatic}[C=C]/\text{aromatic}[C=C])_{polymer}}{(\text{aliphatic}[C=C]/\text{aromatic}[C=C])_{monomer}}\right) \times 100\%$$

All experiments were carried out three times, and the results were analyzed by ANOVA followed by pairwise multiple comparison using Student-Newman-Keuls' multiple range comparison test, with p=0.05 as the level of significance.

Rate of conversion at the initial curing period (up to 5 seconds after curing) was also calculated from the degree of conversion in order to verify which group illustrates the fastest polymerization reaction.

2. Color Stability

Experimental 78% wt. filler loaded composite resin was made by incorporating BisGMA/BisEMA/TEGDMA resin matrix with 3.2% silanated barium glass fillers (mean particle size; 1 um).

FIG. 1 presents composite compositions. The composites were divided into three groups according to resin matrix system for each concentration of photoinitiators (1% and 3%); 1 part CQ and 2 parts of OPPI group (CO) and 1 part of CQ and 2 parts of amine group (CA), and all equally proportioned three components group (COA). Among these groups, 1% CO group was excluded because of its poor polymerization irrespective of over 80 s light curing, which means clinical impracticability. A total of five groups were made and used to examine color stability.

With a white background, resin composites were packed into the disk-shaped mold (Flat Washers, HO1231876, Hillman, USA; 10 mm in diameter and 1.5 mm in thickness) on a cover glass. After packing the composite, another cover glass was pressed on the top of the specimen, and specimens were light-cured each for 60 s with a light-curing unit (Demetron 400, Demetron Research Corp., Danbury, Conn.) with an intensity setting of 440 $mW/cm^2$. Five specimens were used for each color measurement.

Baseline color was measured after immersion in distilled water for 24 h at room temperature and blot dry. CHROMA METER CR-400 (Konica Minolta, Sensing Inc., Japan) was used to measure the CIELAB coordinates of each specimen. The CIE color system (CIELAB) was determined by the International Commission on Illumination in 1978. The three attributes of color in this system are $L^*$, $a^*$, $b^*$, where $L^*$ is the lightness variable proportional to Value in the Munsell system, and $a^*$ and $b^*$ are chromatically coordinates. The $a^*$ and $b^*$ coordinates designate positions on a red/green and yellow/blue axis respectively (+a=red, −a=green; +b=yellow, −b=blue).

To evaluate their color stability, five specimens in each group were put in an empty vial (dry condition) or a vial containing 1% saline solution (wet condition). These vials were kept in 60° C. water bath or dark place at room temperature up to a month. Color coordinates were re-measured one week, 2 weeks, and 4 weeks later. All samples were stored in the dark with no light except when measured.

The color change (ΔE) was calculated using the equation:

$$\Delta E = [(\Delta L^*)^2 + (\Delta a^*)^2 + (\Delta b^*)^2]^{1/2}$$

ΔL, Δa, and Δb are the mathematical differences between baseline $L^*$, $a^*$, $b^*$ and re-measured $L^*$, $a^*$, $b^*$ values. Statistical analysis was done using Kruskal-Wallis and Mann-Whitney tests at a significance level of 0.05.

Results

1. Degree and Rate of Conversion

FIGS. 2 and 3 illustrate the degree of conversion of all groups. Degree of conversion went up with the increased curing time, although, one photoinitiator component groups of 1C and 3C, in which CQ only has been used, showed a very slow and low degree of conversion.

In general, resin monomers including 3% photoinitiator systems converted into polymers more than those containing 1% photoinitiator systems, except CA (CQ and amine system) groups, which showed more rapid and abundant conversion of 1% monomer than 3% monomer.

Of the photoinitiator-component groups, 3COA showed the highest degree of conversion at all curing times. The other groups except 1CO gained similar degrees of conversion when cured more than 60 seconds, while 1COA acquired a greater degree of conversion with relatively shorter curing times (less than 20 seconds).

Figure 4:
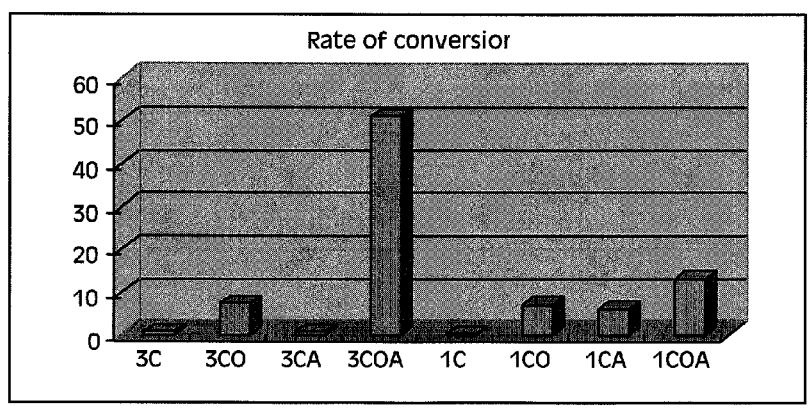
FIG. 4 illustrates the rate of initial conversion (% conversion/sec) of GTE with various photoinitiators.
Figure 7:
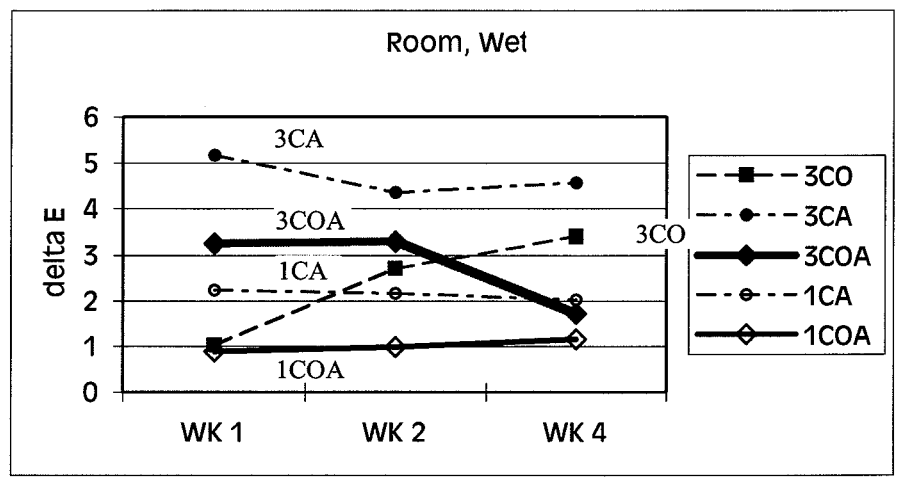
FIG. 7 illustrates the change of $\Delta E$ values with room temperature, wet condition.
Figure 8:
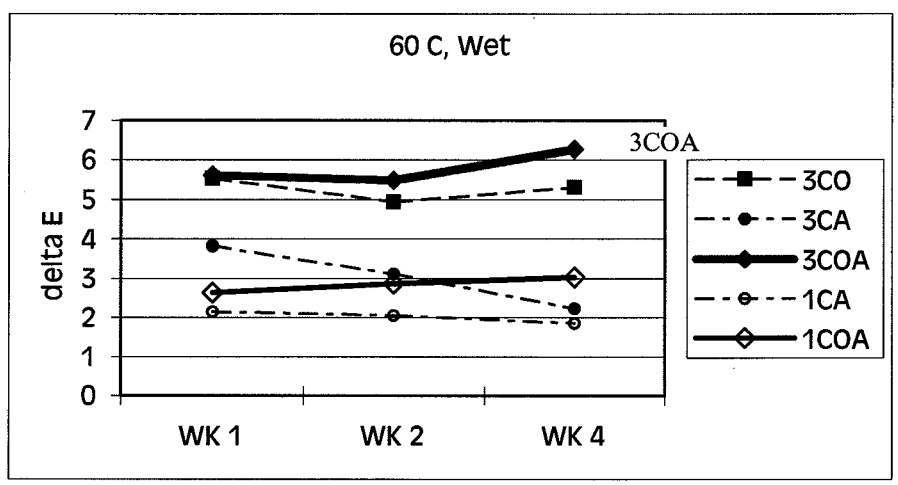
FIG. 8 illustrates the change of $\Delta E$ values with 60° C., wet conditions.
Figure 9:
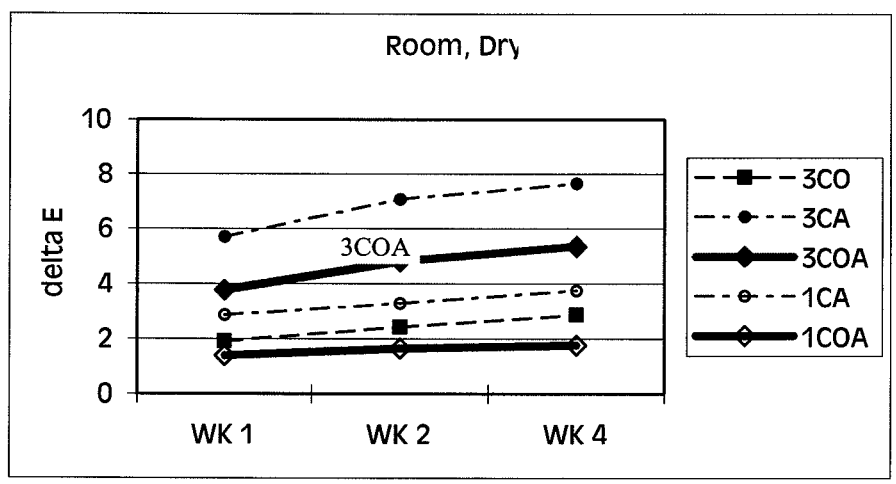
FIG. 9 illustrates the change of $\Delta E$ values with room temperature, dry conditions.
Figure 10:
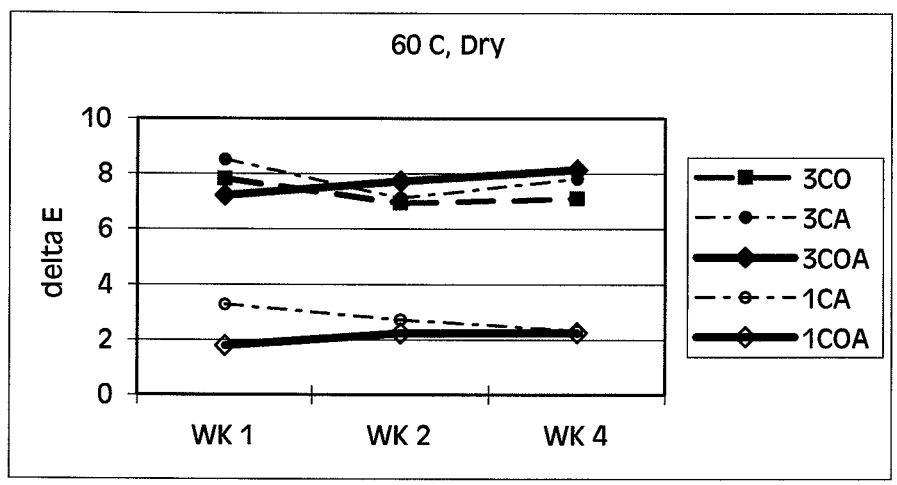
FIG. 10 illustrates the change of $\Delta E$ values with 60° C., dry conditions.
Figure 11:
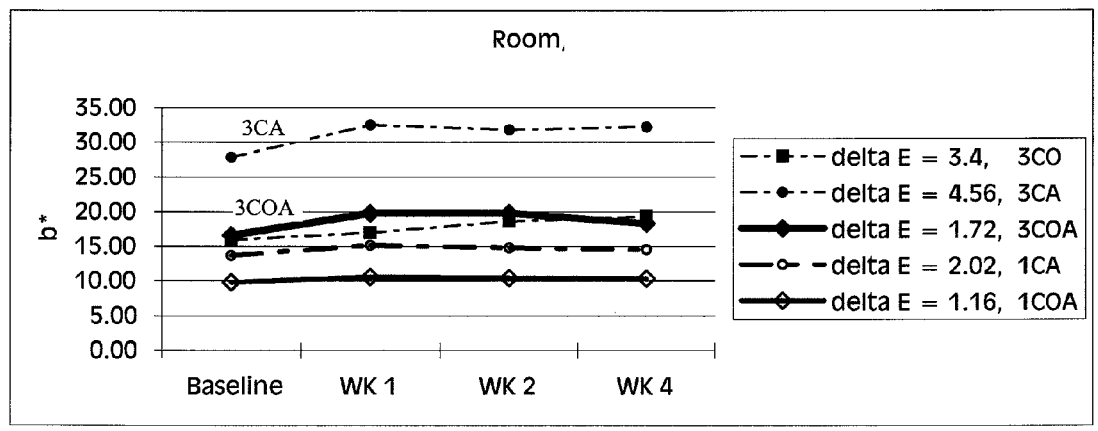
FIG. 11 illustrates the change of $b^*$ values (yellowness) with room temperature and wet conditions.
Figure 12:
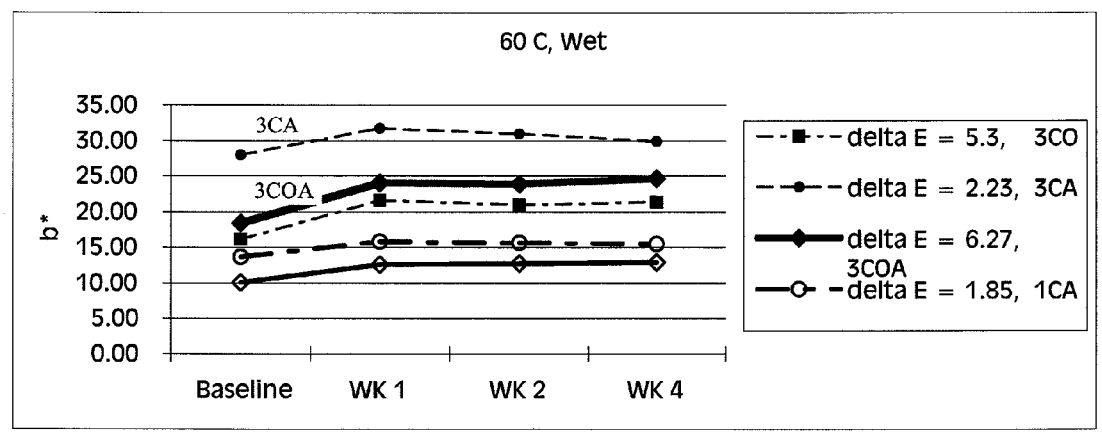
FIG. 12 illustrates the change of $b^*$ values with high temperature and wet conditions.
Figure 13:
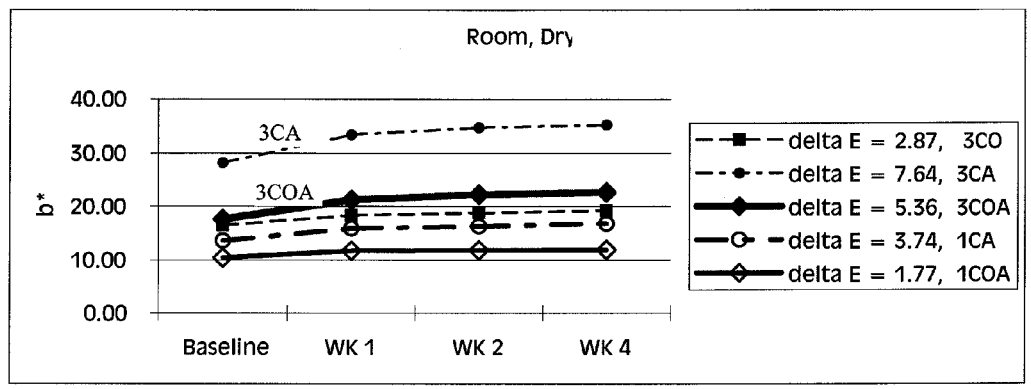
FIG. 13 illustrates the change of $b^*$ values with room temperature and dry conditions.
Figure 14:
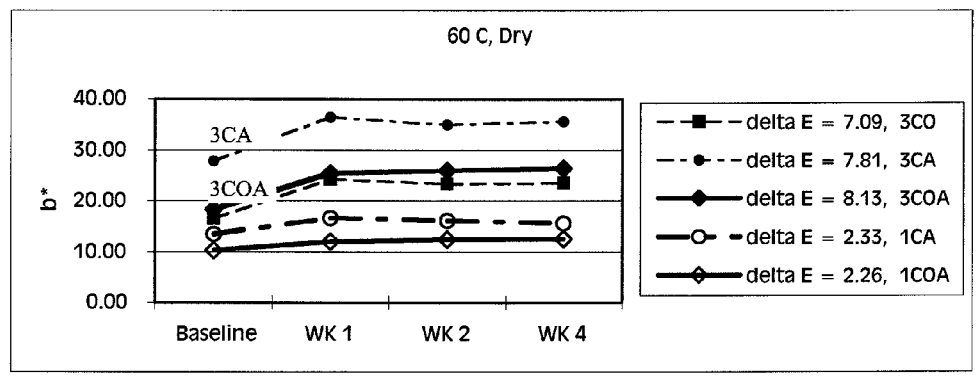
FIG. 14 illustrates the change of $b^*$ values with high temperature and dry conditions.

FIG. 4 illustrates the rate of initial conversion of the groups (rate taken from the five sec curing time interval). The 3COA group showed a faster conversion rate than any of the other groups. Furthermore, the 1COA group showed a faster cure rate than any of the 3% groups.

In summary, CQ photosensitizes OPPI in a blue light photo-cure resin and can substitute for an amine in a CQ/amine photoinitiation system. Also, OPPI acts as a photoinitiator in the presence of CQ. Furthermore, in the presence of CQ, OPPI combined with amine (DMAEMA) increases ultimate conversion and rate of conversion more than OPPI or amine alone.

2. Color Stability

FIG. 5 reveals the change of color coordinates and FIGS. 6-14 illustrate the color change (ΔE) for various process conditions. At baseline, there was no difference in color coordinates among five samples in each group, that is, every specimen has a similar initial color.

When the color coordinates were compared between different concentrations but the same proportions, such as 3CO and 1CO, higher sensitizer and initiator concentrations generally showed darker and/or more yellow colors, and changed more during ageing than did lower photoinitiator concentrations.

From FIG. 5, we can also see the initial color reduction, especially in the b* parameter (3CA-27.95; 3CO-16.25; 3COA-17.71/1CA-13.58; 1COA-10.11), when OPPI has partially or totally replaced the amine. For example, 3CA was darker and more yellow than 3CO and 3COA, and 1CA was more yellow than 1COA.

This tendency continues throughout the experiment. Even after 4 weeks storage in various conditions, the amine-containing 3CA group showed the highest yellow color value although the 3COA group changed a lot more than the 3CA group at the higher temperature with wet and dry conditions. (FIG. 21-24)

Considering the average ΔE for all storage conditions, amine-containing CA groups (3CA-5.56; 1CA-2.49) showed a little bit more color instability than OPPI containing groups (3CO-4.67; 3COA-5.37; 1COA-2.05).

Generally, high temperature (60° C.) or dry conditions brought about more color change than room temperature or wet conditions. Among them, 60° C. and dry combined condition is the harshest, under which composites could not maintain color stability and developed the greatest changes. Room temperature and wet conditions are just the opposite.

In summary, OPPI in place of amine reduces initial color, mainly in the yellow (b*) parameter. In addition, OPPI in place of all or part of the amine has better color stability than the CQ/amine system and resists yellowing, maintaining a value ⅔ to half of that of the CQ/amine system (at the baseline: 3CA-27.86; 3CO-15.96; 3COA-16.60; 1CA-13.67; 1COA-9.81/after 4 weeks: 3CA-32.23; 3CO-19.26; 3COA-18.24; 1CA-14.58; 1COA-10.37).

From the results of this study on degree and rate of conversion and color stability, the following results were obtained.

Substitution of OPPI for the amine provides a faster cure rate, higher conversion, lower initial color and better color stability.

Substitution of OPPI for some or all of both CQ and amine provides very low initial color and exceptional color stability.

Discussion

The organic formulations of dental composite resins include photoinitiation systems that absorb light and excite the molecules to higher energy states. From there, free radicals or other initiating species form and initiate conversion of oligomer blends to a polymeric crosslinked network.

Proper combination of light source, exposure time and photo-sensitizer/co-initiator systems are regarded as major factors to optimize light curing of dental composites, because improved conversion is critical for the optimization of mechanical properties, clinical performance and longevity, and biocompatibility.

CQ combined with active-hydrogen amines is the most commonly used photoinitiator system for dental composites because it has a light absorption maximum at 468 nm, which matches well with Quartz-halide dental curing lamps. However, it has some drawbacks such as low polymerization efficiency and toxicity. The photolysis of a diketone leads to the homolytic cleavage of the C—C bond between the two carbonyl groups, resulting in two carbonyl radicals. This radical pair can undergo cage escape to form photo-decomposed products. However, the two carbonyl radicals in CQ are structurally connected to each other and the probability of their recombination in CQ is great. The consequent low polymerization efficiency of CQ results in relatively low mechanical properties without relatively high CQ concentrations and/or relatively long exposure times, as well as possible toxic effects from unreacted residual monomers.

In this study, experimental groups "C," which used CQ alone as both photosensitizer and photoinitiator, showed very low degrees of conversion even after 300 seconds exposure (1C-3.36%; 3C-23.57%).

High degrees of conversion could not be obtained until CQ was combined with an amine (1CA-56.93%; 3CA-52.12% at 300 seconds). The irradiation of the diketone and amine mixture resulted in the formation of an exciplex (excited state complex) via an electron transfer from amine to excited ketone. A hydrogen transfer from hydrogen of amine to the diketone in the exciplex resulted in the production of an aminyl radical and a hydryl radical. The aminyl radical is responsible for the initiation of the polymerization reaction, whereas the CQ hydryl radical is almost inactive. The photodecomposition rate of CQ increases with the addition of amine.

It is well known that high concentrations of CQ in resin formulations results in undesirable photo-yellowing effects and a poor aesthetic appearance for the cured material. Therefore, there have been numerous efforts to enhance the photoinitiator efficiency at lower concentrations by adding different co-initiators.

In the present study, OPPI (p-octyloxy-phenyl-phenyl iodonium hexafuoroantimonate) was used as an additional or alternative photoinitiator to enhance the degree and rate of conversion and, furthermore, to overcome the color problems associated with CQ. It was noted that the optimal photosensitizer/co-initiator concentration depends on many factors such as solubility of these compounds in the monomer mixture, absorption characteristics of the sensitizer, photo-reactivity (ability to form free radicals when the photosensitizer and co-initiator react), the effects of these compounds on color, the overlap between the wavelengths of light-source emission and photosensitizer absorption, and the biocompatibility of the components in the photoinitiator system.

OPPI is an organic-soluble white onium salt and can be used as a somewhat hybrid photoinitiator, designed to be able to induce not only cationic polymerization, but free radical polymerization as well. The onium salt immediately decomposes forming phenyl radicals, which may initiate cure or, abstract a hydrogen from the amine or monomer forming initiating radicals, therefore, it has sufficient energy to initiate the free-radical polymerization.

OPPI alone has an absorption maximum around 300 nm with a tail out to 380 nm, which is not in accord with the irradiated wavelengths from the conventional dental curing lamps. However, It was informed that the use of photosensitizers is one of the approaches to extend its absorption to longer wavelength ranges by forming bimolecular photosensitization systems with onium salts although the efficiency of bimolecular systems are usually limited by diffusion, especially in highly viscous polymeric systems. For instance, combined, the borate/OPPI complex exhibits a substantial shift of 50 nm towards the visible light, which extends the tail of the absorbance to about 440 nm.

Of all the experimental groups, 3COA showed the highest degree and the fastest rate of conversion during all the curing time. While, 1COA acquired similar degree of conversion to that of conventional 1CA group [(1COA): 43.95%, 48.24%, 53.64%; (1CA): 40.65%, 49.96%, 56.93% at the times of 40, 60, 300 seconds], however, more degree of conversion was obtained within a relatively short time [(1COA): 13.24%, 32.08%; (1CA): 6.02%, 20.11% at the times of 5, 20 seconds].

These results indicate that OPPI combined with amine increases ultimate conversion and rate of conversion more than OPPI or amine alone in the presence of CQ.

Resin monomers with the higher concentration of photoinitiator systems (3%) showed greater conversion than those containing the lower concentration (1%). This result implies that improved converted composite resins with optimized mechanical properties can be obtained by using higher concentrations of the photoinitiator system if color problems and accompanying possible polymerization shrinkage could be mitigated.

Ideally, a composite resin should have the same color and translucency as tooth structure in order to achieve a perfect color match between tooth and restoration. This is currently one of the more demanding factors in restorative dentistry. In addition, one of the most common reasons for replacing restorations is esthetic failure; therefore, color stability is another important factor.

As mentioned above earlier, composite resin with large amounts of CQ will create undesirable photo-yellowing effects. Similarly, high concentrations of photoinitiator (3%) show darker and/or more yellow color and change more during ageing than do resins with lower photoinitiator concentrations (1% in this study).

However, when compared with monomers containing CQ and amine, the initial color reduction, especially in b* parameter (3CA-27.95; 3CO-16.25; 3COA-17.71/1CA-13.58; 1COA-10.11) is gained if OPPI is present. That is, if OPPI has either partially or totally replaced the amine initiator. For example, 3CA [L*, a*, b*: 84.16, −1.00, 27.95] was darker and more yellow than 3CO [L*, a*, b*: 87.20, −3.90, 16.25] and 3COA [L*, a*, b*: 86.86, −3.75, 17.71] and 1CA [L*, a*, b*: 87.08, −1.74, 13.58] was more yellow than 1COA [L*, a*, b*: 88.09, −2.09, 10.11]. Even after 4 weeks storage in various conditions, amine-containing 3CA (33.23) showed the highest yellow color value (3CO-20.83; 3COA-22.97) although 3COA changed a lot more than 3CA at the higher temperature in a wet environment [ΔE: 3COA-6.27; 3CA-2.23] and under dry conditions [ΔE: 3COA-8.13; 3CA-7.81] (FIGS. 21-24). Furthermore, the OPPI-containing groups (ΔE: 3CO-4.67; 3COA-5.37; 1COA-2.05) showed somewhat more color stability than the amine-containing CA groups (ΔE: 3CA-5.56; 1CA-2.49), when considering average ΔE of all storage conditions.

High temperature or dry conditions brought about more color change than room temperature or wet conditions. Among them, combined high temperature and dry conditions has the greatest effect (ΔE: 5.52), in which the composite has the least color stability (greatest increase in color). The combination of room temperature and wet conditions has just the opposite effect (ΔE: 2.57, the least color change).

Even though very promising results, such as increased rate and extent of monomer conversion, and increased color stability, can be obtained by using OPPI as a photoinitiator, other factors, such as biocompatibility, proper proportion, and/or the like, should also be considered. Generally, aqueous extracts of cured resins are reported to be less cytotoxic than aqueous extracts of the individual components. This means that the individual components may have been well polymerized and incorporated into the resin formulation such that elution of leachables does not reach toxic levels for the individual components. However, the widely used BisGMA oligomer has been found to be somewhat cytotoxic in many cell culture systems and there is a report that the photoinitiator Sarcat™ CD 1012, a diaryliodonium salt with a structure similar to OPPI, has greater cytotoxicity [$TC_{50}$=14 mM] than CQ [$TC_{50}$=779 mM].

A decreased degree of conversion can result if insufficient amine is used, and in addition, resin color instability is aggravated and residual color problems develop at higher onium levels.

Only two values of total concentration (1%, 3%) and four proportions of the CQ/OPPI photoinitiator systems were investigated in this study. Therefore, the biocompatibility of composite resins containing OPPI, optimum concentrations and proper proportion of the three components (CQ/OPPI/amine), and other, additional, photosensitizers, photoinitiators, and co-initiator amines should be the subject of further studies.

Within the limits of this study, the following may be hypothesized:

OPPI can be used to replace the amine in a given CQ/amine photoinitiator system to accelerate cure rate, increase conversion, reduce initial color and increase color stability.

OPPI can be included with CQ and amine to allow reduction in CQ and amine concentration while maintaining or improving rate and degree of conversion and producing a very low color (e.g., b* value: 10) with improved color stability.

Including OPPI as a co-initiator with CQ and amine provides an increased range of trade-offs and flexibility of choice among curing and esthetic characteristics.

Example 3

Novel photoinitiator systems to improve rate and degree of double-bond conversion in both BisGMA-based conventional monomers and low-shrinkage experimental monomer resins Issue 3

To determine the effects of the combination of p-octyloxyphenyl-phenyl iodonium hexafuoroantimonate (OPPI) with other initiators and photosensitizers on the degree of conversion (DC) and volumetric shrinkage of a BisGMA-based composite resin (GTE) and a low-shrinkage liquid crystal monomer (LCM) based composite resin.

Methods

Samples were made with various ratios of photosensitizers (camphorquinone [CQ] and/or 1-phenyl 1,2-propanedione

[PPD]) and photoinitiators (OPPI and/or 2-dimethylaminoethyl methacrylate [DMAEMA]). Half of the samples were of GTE, a BisGMA-based composite resin (BisGMA/TEGDMA/BisEMA [37.5:37.5:25 by % wt]), and the other half were of a LCM-based composite resin (C6-tbutyl-dimethacrylate). The use of PPD is elaborated in U.S. Pat. No. 6,204,302, "Photosensitizers for free radical polymerization initiation resins, and method of making the same."

Each monomer was polymerized using a halogen curing unit (COE LunarTA Cure Unit, GC America Inc., Alsip, Ill.) with an intensity of 200 mW/cm$^2$ for 10 s, 20 s, 40 s, 80 s, 120 s, 240 s and their degree of conversion levels (DC) were determined at each curing time with Fourier transform infrared spectrophotometer (FTIR).

To determine shrinkage, each monomer was cured using the same curing unit for 180 s. After 20 minutes, the difference between the uncured and cured volumes was determined with the Acuvol (Bisco Inc., Schaumburg, Ill.).

Results

Samples containing 1% OPPI by mass showed significant increases in polymerization rate and maximum DC for both GTE-based and LCM-based resins. OPPI functions best in the presence of an amine. OPPI does not seem to significantly affect shrinkage. Neither shrinkage nor DC was dependent upon the ratios of CQ to PPD.

OPPI can be used in conjunction with other photoinitiator systems in both GTE and LCM-based resins to significantly increase both rate of conversion and maximum DC, functioning best when an amine (DMAEMA) is present as a coinitator.

OPPI can be used in this manner in LCM-based resins, and perhaps also in GTE-based resins, without significantly affecting shrinkage.

Varying the proportions of CQ and PPD used in conjunction with OPPI and/or DMAEMA (while keeping CQ+PPD at 1% of the resin by weight) has no significant effect on degree of conversion or rate of conversion in GTE and LCM systems and has no significant effect on shrinkage in LCM systems.

Materials and Methods

The first part of the DC experiment focused on the effect of using OPPI in conjunction with existing photosensitizer/photoinitiator systems (DMAEMA plus CQ and/or PPD). A total of 16 groups were prepared (all by % wt).

FIG. 15 illustrates various GTE monomer mixtures was made by mixing 37.5 wt % BisGMA (lot #568-21-07, ESSTECH, Essington, Pa.), 37.5 wt % BisEMA (lot #474-32-02, ESSCHEM Inc. Linwood, Pa.), and 25 wt % TEGDMA (lot #597-23-02, ESSTECH).

FIG. 16 illustrates various LCM monomer (C6-tbutyl-dimethacrylate) mixtures comprised as disclosed.

The second part of the DC experiment focused on OPPI's ability to increase DC without the presence of other coinitiators. Three groups were prepared for this part as is illustrated in FIG. 17.

1. Degree and Rate of Conversion

Degree of conversion (DC) was determined with a Fourier transform infra-red (FTIR) spectrophotometer (Nicolet Magna-IR Spectrophotometer 550, Thermo Electron Corp, Boston, Mass.) with an attenuated total reflectance (ATR) attachment (Miracle Single Reflection ATR, Pike Technologies, Madison, Wis.). A small amount of uncured resin was placed on the ATR crystal, a spectrum was collected, and the monomer was cured with a halogen curing unit (COE LunarTA Cure Unit, GC America Inc., Alsip, Ill.) with an intensity of 200 mW/cm2 for 10 s, after which another spectrum was collected, and so on. Spectra were collected after 10 s, 20 s, 40 s, 80 s, 120 s, 240 s of total curing time.

Rate of conversion (in % per second) was calculated from the DC after ten seconds of cure (conversion rate was assumed to be linear during the first ten seconds of cure).

Each mixture was tested three times, and results were analyzed by ANOVA with a significance level of 0.05.

Shrinkage was determined for the LCM and OLCM samples. A small amount of monomer was placed on the pedestal of an Acuvol™ image analyzer (Bisco Inc., Schaumburg, Ill. Its volume was measured, then the monomer was cured for 180 s to reach maximum DC. Since curing the specimen increases its temperature which results in thermal expansion, twenty minutes were allowed to elapse to let the specimen cool down to room temperature before the volume was measured again and the shrinkage was determined. Results were analyzed by ANOVA with a significance level of 0.05.

Results

1a. Degree and Rate of Conversion, part 1

Addition of OPPI to GTE-based and LCM-based resins created a significant increase in both maximum DC and initial conversion rate. FIGS. 18, 19, 21, and 22 contain the DC after each cure time. The number after the hyphen in the first column indicates the trial.

From FIG. 18, one of ordinary skill in the art can note that the missing DC's denote unusable FTIR spectra because of peak deformation at the aliphatic peak. Since relatively little conversion occurs between 80, 120, and 240 secs, the highest usable value of these three cure times was selected as the maximum DC. If all three of these values are unavailable for a particular trial, then that trial (shown in white text with black background) was discarded for maximum DC analysis (but retained for initial conversion rate analysis).

Figures 19, 20:
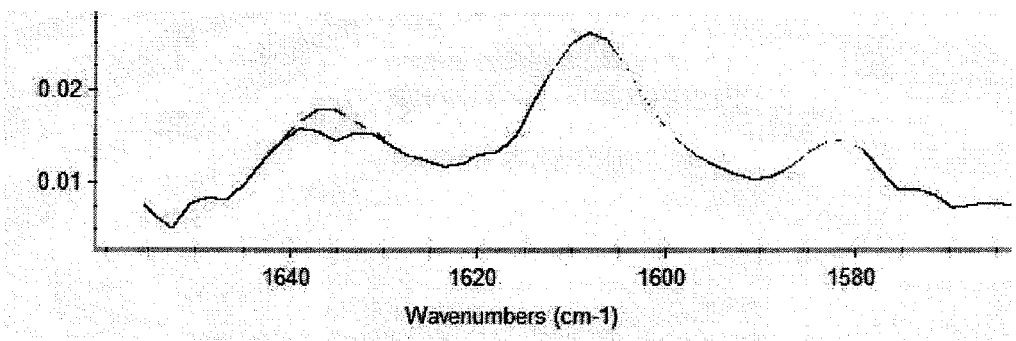
FIG. 19 illustrates the DC of OGTE (GTE with OPPI added to the initiator system) samples.
FIG. 20 illustrates the peak deformation at the aliphatic C=C peak.

FIG. 20 illustrates peak deformation at the aliphatic C=C peak. The supposed approximate location of the peak is denoted by the dotted lines. Since the actual peak height is indeterminable, spectra with this characteristic are unusable and were discarded for maximum DC analysis.

Since no significant change in terms of curing occurred when varying the ratios of CQ to PPD in the resin composite, all GTE samples were grouped together, all OGTE were grouped together, and all LCM and OLCM samples were similarly grouped for the purposes of ANOVA analysis. Therefore, this experiment can be viewed as having four groups (GTE, OGTE, LCM, OLCM), with each group having 9-15 trials.

Figure 23:
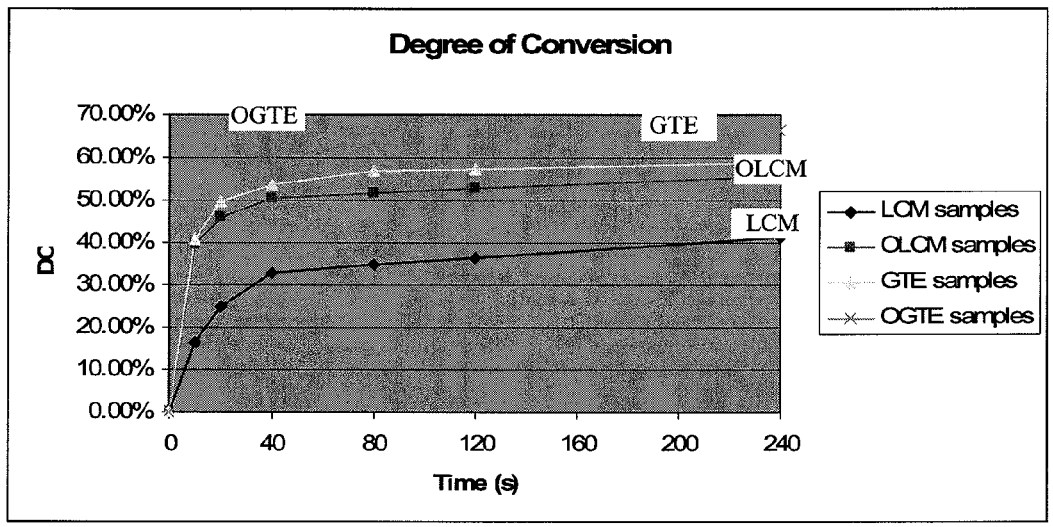
FIG. 23 illustrates the line graph comparing the average DC at each curing time for GTE, OGTE, LCM, OLCM samples.
Figure 24:
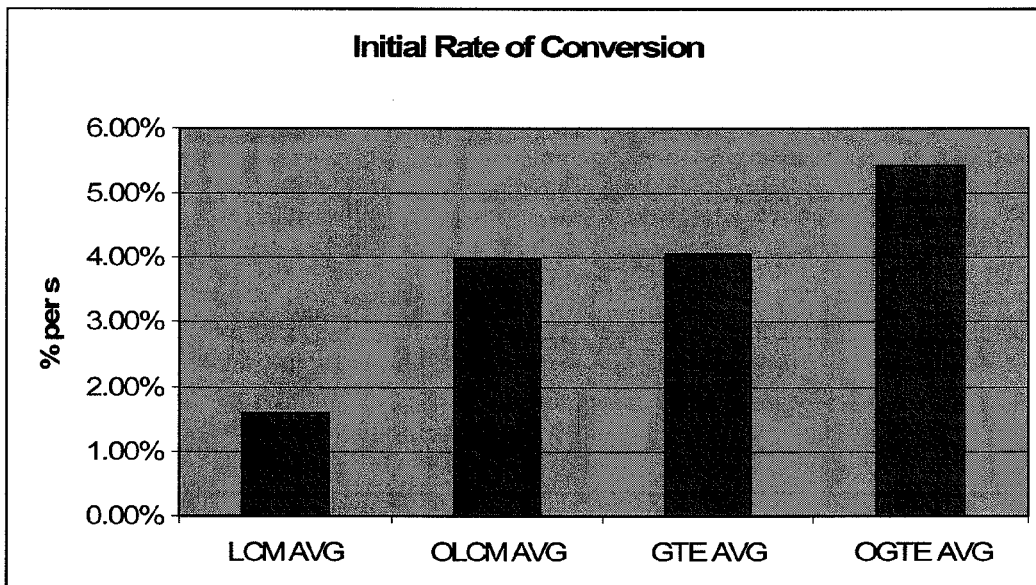
FIG. 24 is the graph showing initial conversion rate (determined from the first 10 seconds of cure).

From the data presented in the figures including, but not limited to, FIGS. 23 and 24, it is evident that GTE has an inherently higher maximum attainable DC and initial conversion rate than LCM. However, the OLCM samples exhibited DC's and conversion rates comparable to those of normal GTE (without OPPI). Addition of OPPI increases maximum DC in GTE samples by about 10% and in LCM samples by about 33%. Addition of OPPI increases initial conversion rate in GTE by about 33% and in LCM by over 140%.

1b. Degree and Rate of Conversion, part 2

Figures 25, 26:
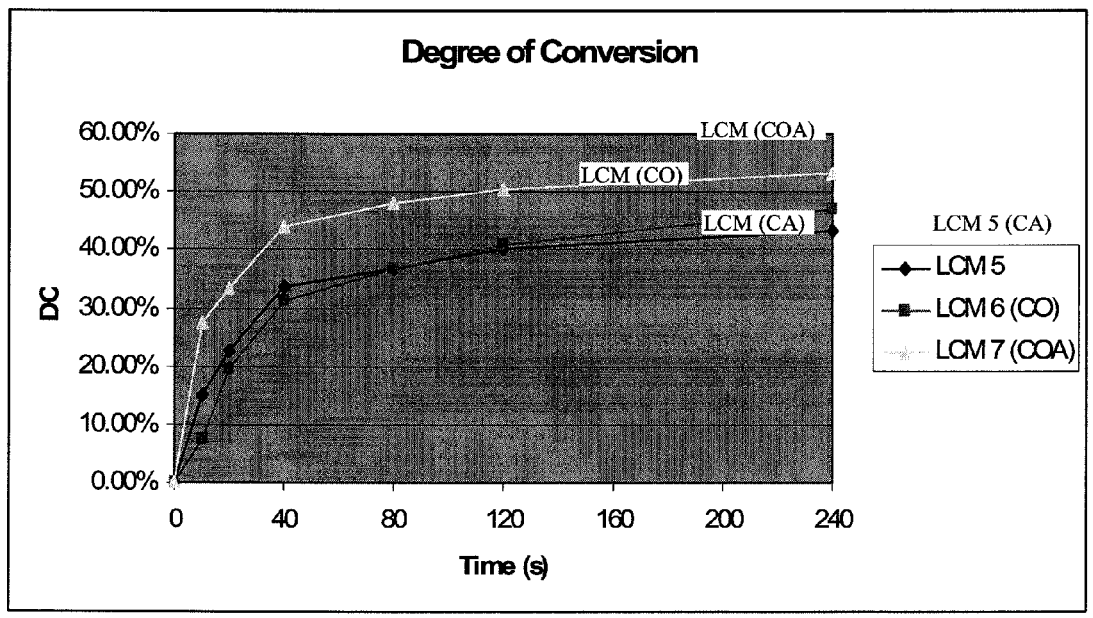
FIG. 25 illustrates the DC of LCM samples for part 2 of DC analysis.
FIG. 26 illustrates the line graph comparing average cure rates of LCM 5, 6, and 7.
Figures 27, 28, 29:
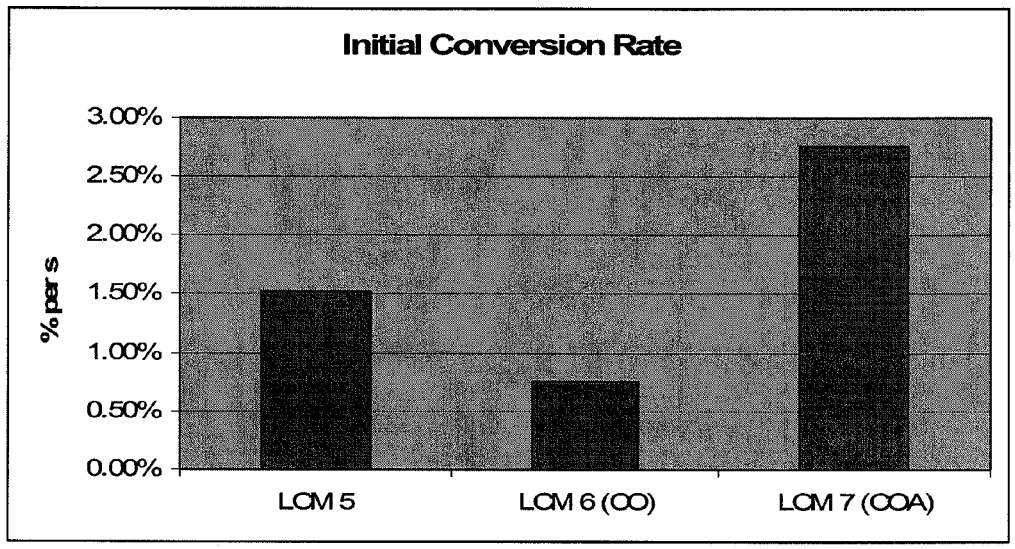
FIG. 27 illustrates Initial conversion rate of LCM 5, 6, and 7 (determined from the first 10 seconds of cure).
FIG. 28 illustrates the shrinkage analysis determined by image analysis using and Acuvol™.
FIG. 29 illustrates the shrinkage averages—LCM vs. OLCM samples.

FIGS. 25-27 illustrate a comparison of LCM samples 5, 6, and 7 found that DC and initial conversion rate are highest in LCM7, where CQ is present as the photosensitizer, and OPPI and DMAEMA (amine) are present as photoinitiators.

2. Shrinkage

FIG. 28 illustrates a shrinkage analysis carried out only in the LCM-based resins.

FIG. 29 illustrates that no significant change occurred when varying the ratios of CQ to PPD in the resin composite, all LCM samples were grouped together and all OLCM were grouped together. Therefore, this part of the experiment can be viewed as having two groups (LCM, OLCM), with each group having 9 trials.

Although the OLCM samples had nominally higher shrinkages than the LCM samples, ANOVA analysis showed no statistical significance.

Within the context of this experiment, it can be hypothesized that:

OPPI can be used in conjunction with other photosensitizer/photoinitiator systems (DMAEMA plus PPD and/or CQ) in both GTE-based and LCM-based resins to significantly increase both rate of conversion and maximum DC, functioning best when in the presence of an amine (DMAEMA) coinitiator.

OPPI can be used in this manner in LCM-based resins, and perhaps also in GTE-based resins, without significantly affecting shrinkage.

Varying the proportions of CQ and PPD used in conjunction with OPPI and/or DMAEMA (while keeping CQ+PPD at 1% of the resin by weight) has no significant effect on degree of conversion or rate of conversion in GTE and LCM systems and has no significant effect on shrinkage in LCM systems.

Example 4

This example illustrates the effect of a hydroperoxide oxidizing agent and substituted thiourea concentrations on degree of cure, color and color stability of self-cure systems in a conventional BisGMA/TEGDMA/BisEMA (GTE) monomer blend system.

Issue 4

To determine the effect of hydroperoxide oxidizing agent and substituted thiourea concentrations on degree of cure, color and color stability of self-cure systems in a conventional GTE monomer blend system.

Methods

Monomer mixture was made by mixing 37.5 wt % BisGMA (lot #568-21-07, ESSTECH, Essington, Pa.), 37.5 wt % BisEMA (lot #474-32-02, ESSCHEM Inc. Linwood, Pa.), and 25 wt % TEGDMA (lot #597-23-02, ESSTECH). To this were added different concentrations of the cumene hydroperoxide (3.73-18.67 wt %) and allyl thiourea (2.1-10.5 wt %) (Sigma-Aldrich). 2.1 wt % of thiourea and 3.73 wt % of cumene hydroperoxide were considered to be a 1:1 ratio.

The two parts were mixed and cured into disc-shaped specimens ⅜" in diameter and 1/16" thick. After 24 hours, the samples were tested for hardness as a measure of degree of cure using a 306L Durometer D-scale indenter.

Color stability was evaluated using a Konica Minolta Chroma Meter CR-400 to record CIE L*a*b* color parameters during accelerated aging in which samples were stored in water at 60° C. for 6 weeks. Changes in overall color, $\Delta E^*$, and in the yellow-blue coordinate, $b^*$, were determined weekly.

Results

Figure 30:
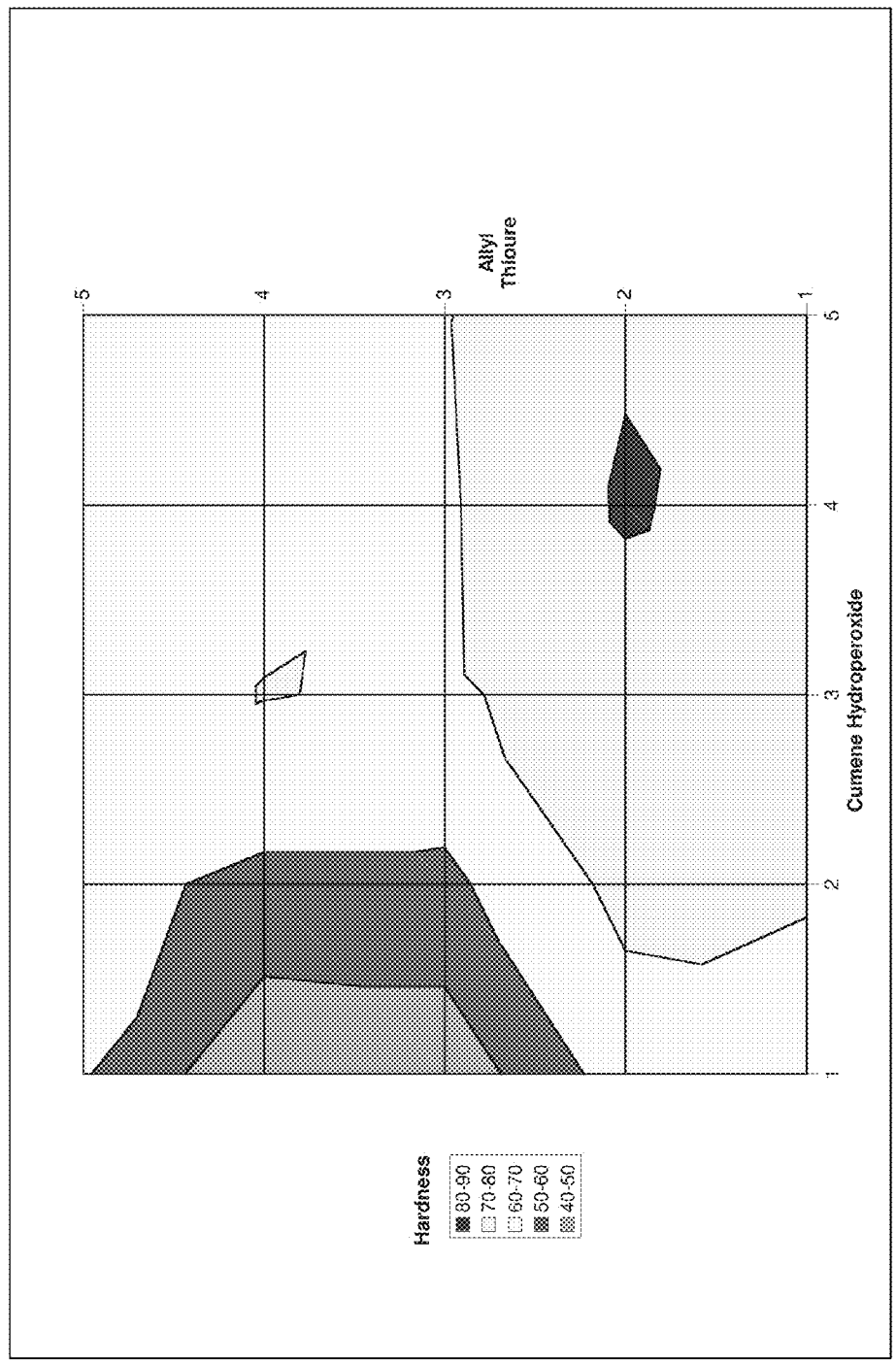
FIG. 30 illustrates the durometer hardness of low color self-cure resins.

FIG. 30 illustrates a surface plot of hardness with respect to Allyl Thiourea (T):Cumene hydroperoxide (C) ratio. The ratio of 2T:4C was found to be the hardest self-cure measuring 81.1±2.09 on the durometer scale. These self-cures had lower hardness than the GTE control light-cures (83.8±1.39).

Figure 31:
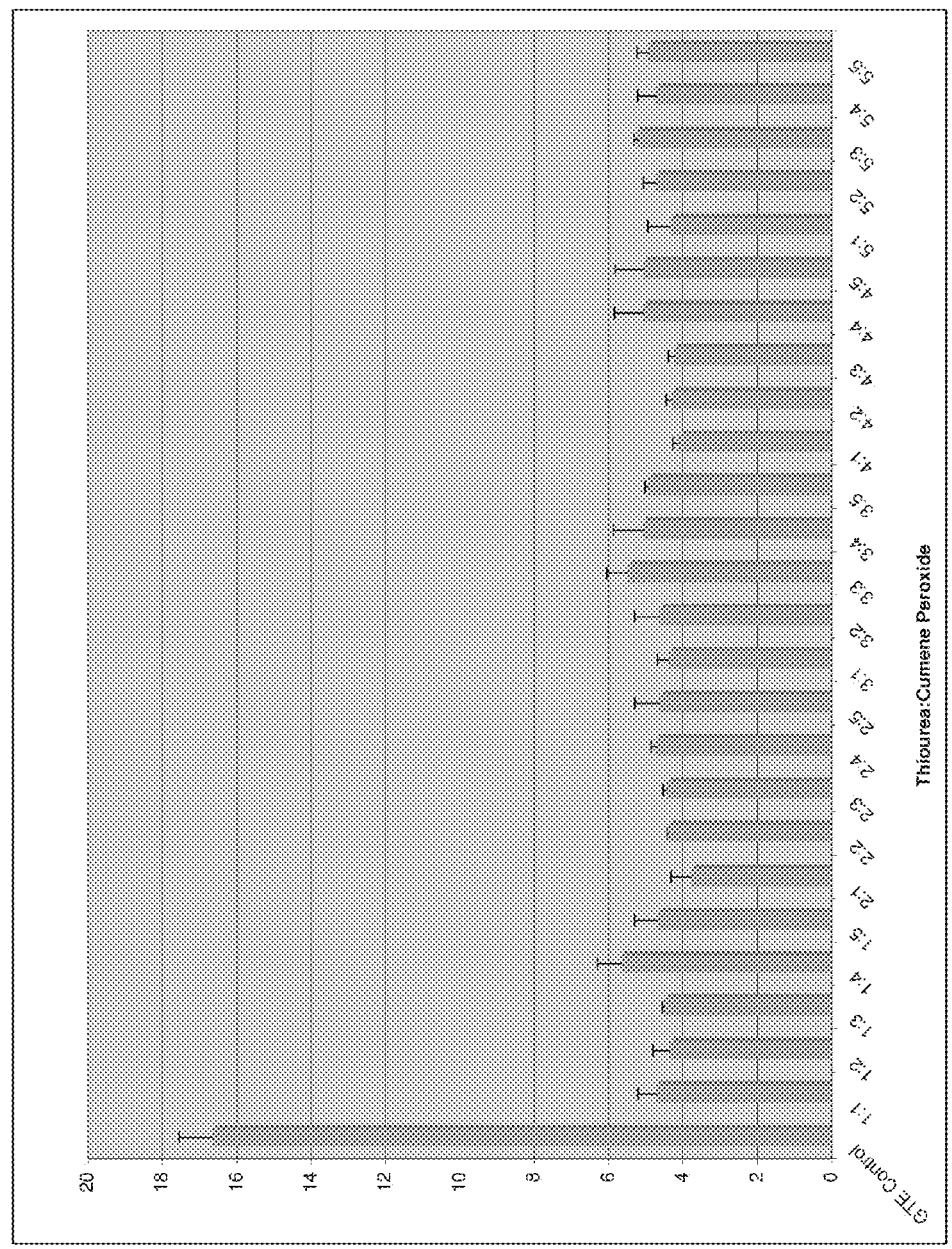
FIG. 31 illustrates the initial $b^*$ of self-cure resins.

FIG. 31 illustrates initial yellowness of the resins. Initially all self-cured resins were much lower color than GTE controls. $b^*$ values were used instead of $L^* a^* b^*$ because most of the color change was observed in the $b^*$ range.

Figure 32:
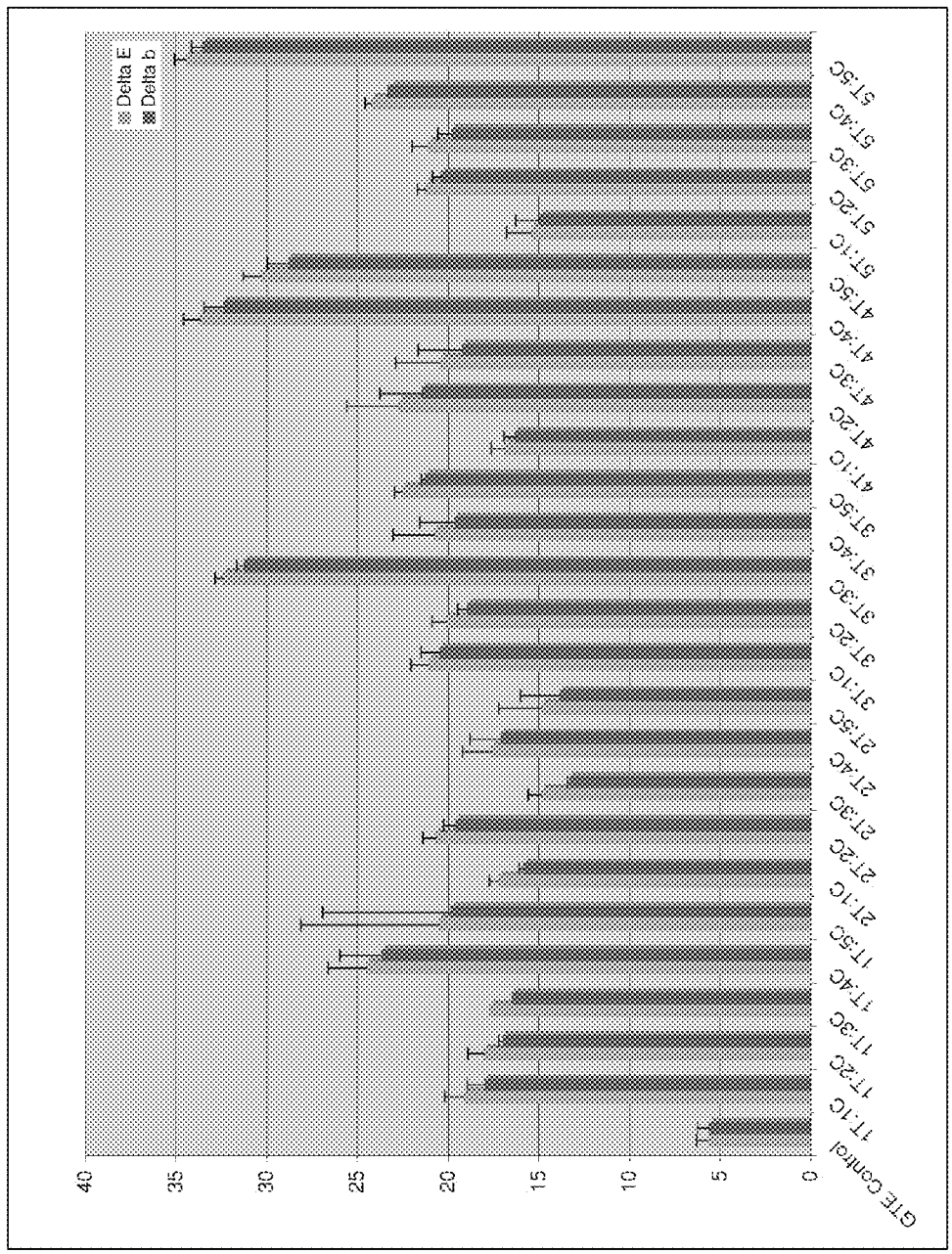
FIG. 32 illustrates the color stability of self-cure resins after 5 weeks.

FIG. 32 illustrates the color stability of self-cured resins. $\Delta E^* > 3.3$ is clinically detectable. All resins had clinically noticeable color change and most of $\Delta E^*$ can be accounted for by $\Delta b^*$, i.e. the shift in the yellowness of the resin. While all the self-cures had much lower initial color, they are much less color-stable than the light-cured GTE control and only eight self-cure formulations had final $b^*$ values that were comparable to or lower than the GTE control (1T:1-3C; 2T:1, 3, 5C; 4T:1C & 5T:1C). These were also the formulations that had the lowest $\Delta b^*$. When the data is considered in the perspective that self-cures are generally much more yellow and much less color stable than light-cured resins like the GTE control used here, these results indicate a significant improvement in the color and color stability over conventional self-cured systems.

Self-cured resins using allyl thiourea and cumene hydroperoxide have lower initial color than even conventional light-cured systems. The final color of self-cures were comparable or less colored than light-cured systems. However, the color shift of self-cures was significantly higher than that of GTE controls and their hardness was also not as high. The lower degree of cure seems to be a good indicator of color stability as shown in other results below. From these results, combinations that did not produce a suitable cure were discarded and ratios in the range from IT:1C to 3T:5C were chosen for further investigation for use as the self-cure part in a dual-cure system using camphor quinone (CQ) as the photoinitiator and 2-dimethylaminoethyl methacrylate (DMAEMA) as the amine co-initiator.

Example 5

Issue 5

To determine the effect of hydroperoxide oxidizing agent and substituted thiourea concentrations on degree of cure, color and color stability of dual-cure systems in a GTE system containing camphor quinone (CQ) as the photoinitiator and 2-dimethylaminoethyl methacrylate (DMAEMA) as the amine co-initiator.

Methods

To the same monomer mixture used in ISSUE 1 were added different concentrations of cumene hydroperoxide (3.73-18.67 wt %) and allyl thiourea (2.1-6.3 wt %) (Sigma-Aldrich). Again, 3.5 wt % of thiourea and 2.1 wt % of cumene hydroperoxide were considered to be a 1:1 ratio. This was then blended with a similar monomer mixture that contained CQ (1 wt %) and DMAEMA (2 wt %) in ratios of 50:50 or 75:25 (self-cure:light-cure). This mixture was light-cured into disc-shaped specimens ⅜" in diameter and 1/16" thick.

After 24 hours, the samples were tested for hardness as a measure of degree of cure. Initial color and color stability in water at 60° C. for 6 weeks as done in ISSUE 1.

Results

Figure 33:
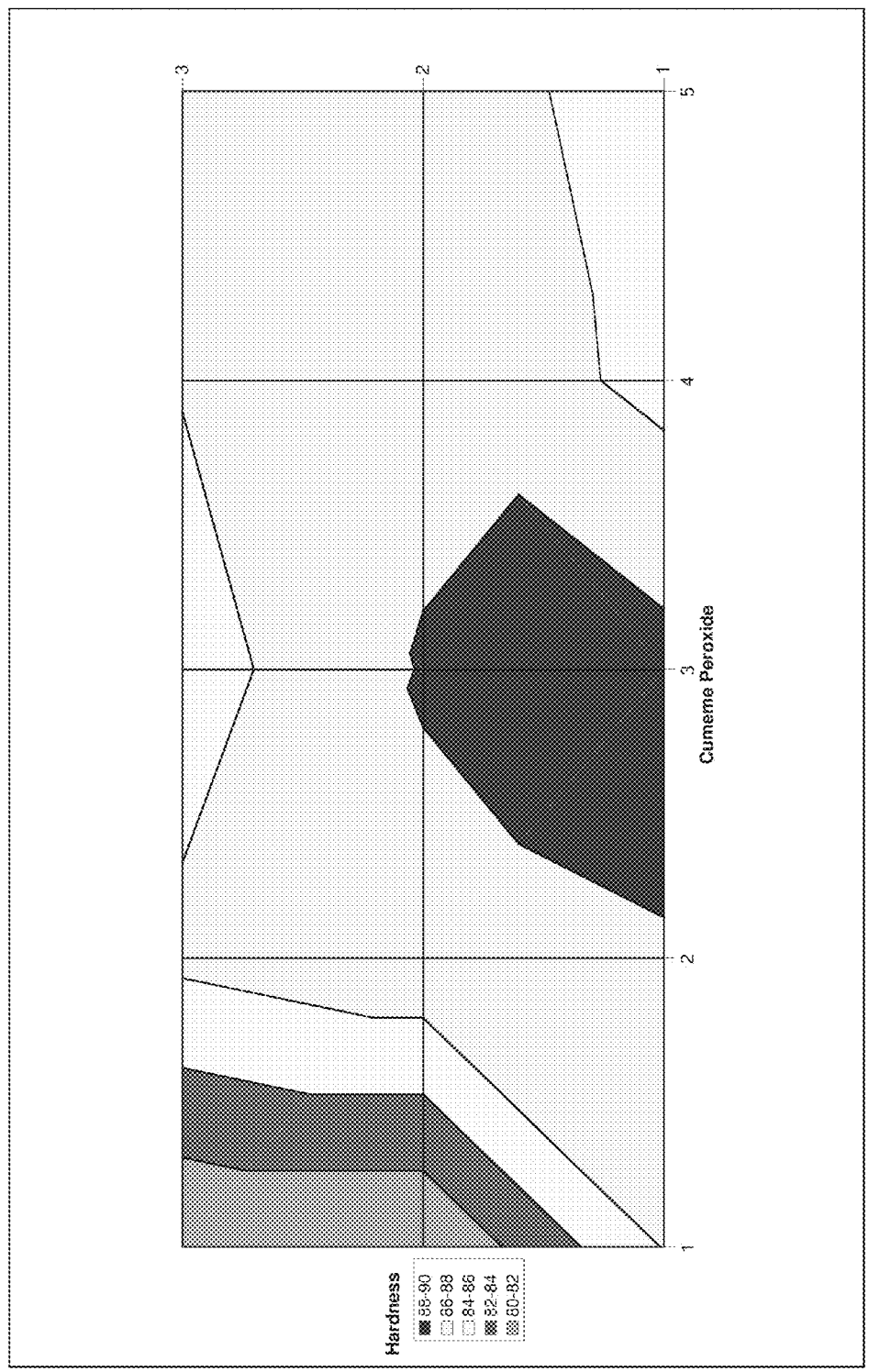
FIG. 33 illustrates the durometer hardness of 50:50 (self: light) dual-cure resins with 1% camphorquinione (CQ) and 2% 2-dimethylaminoethyl methacrylate (DMAEMA).

FIG. 33 illustrates a surface plot of hardness with respect to T:C ratio for 50:50 (self:light) dual-cure resins. The ratios of 1T:3C and 2T:3C were found to be the hardest dual-cures measuring 88.7±1 and 88.1±1.45, respectively, on the durometer scale. These dual-cures had higher hardness than the GTE control light-cures (83.8+1.39).

Figure 34:
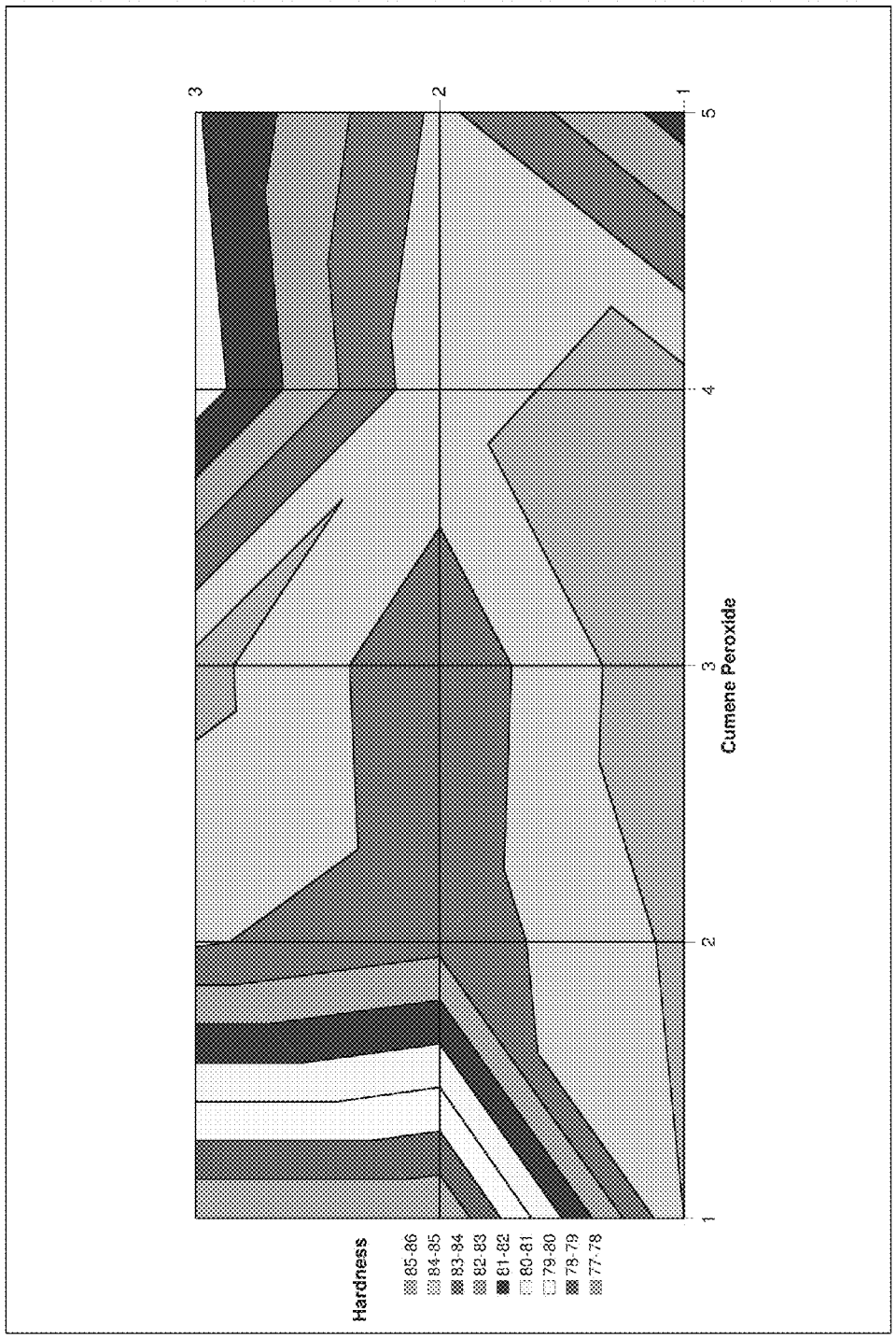
FIG. 34 illustrates the durometer hardness of 75:25 (self: light) dual-cure resins with 1% CQ and 2% DMAEMA.

FIG. 34 illustrates a surface plot of hardness with respect to T:C ratio for 75:25 (self:light) dual-cure resins. The ratios of IT:1C to 1T:4C and 3T:3C were found to be the hardest dual-cures measuring in the 85 range on the durometer scale. These dual-cures had lower hardness than 50:50 dual-cures but they were still higher than the GTE control light-cures.

Figure 35:
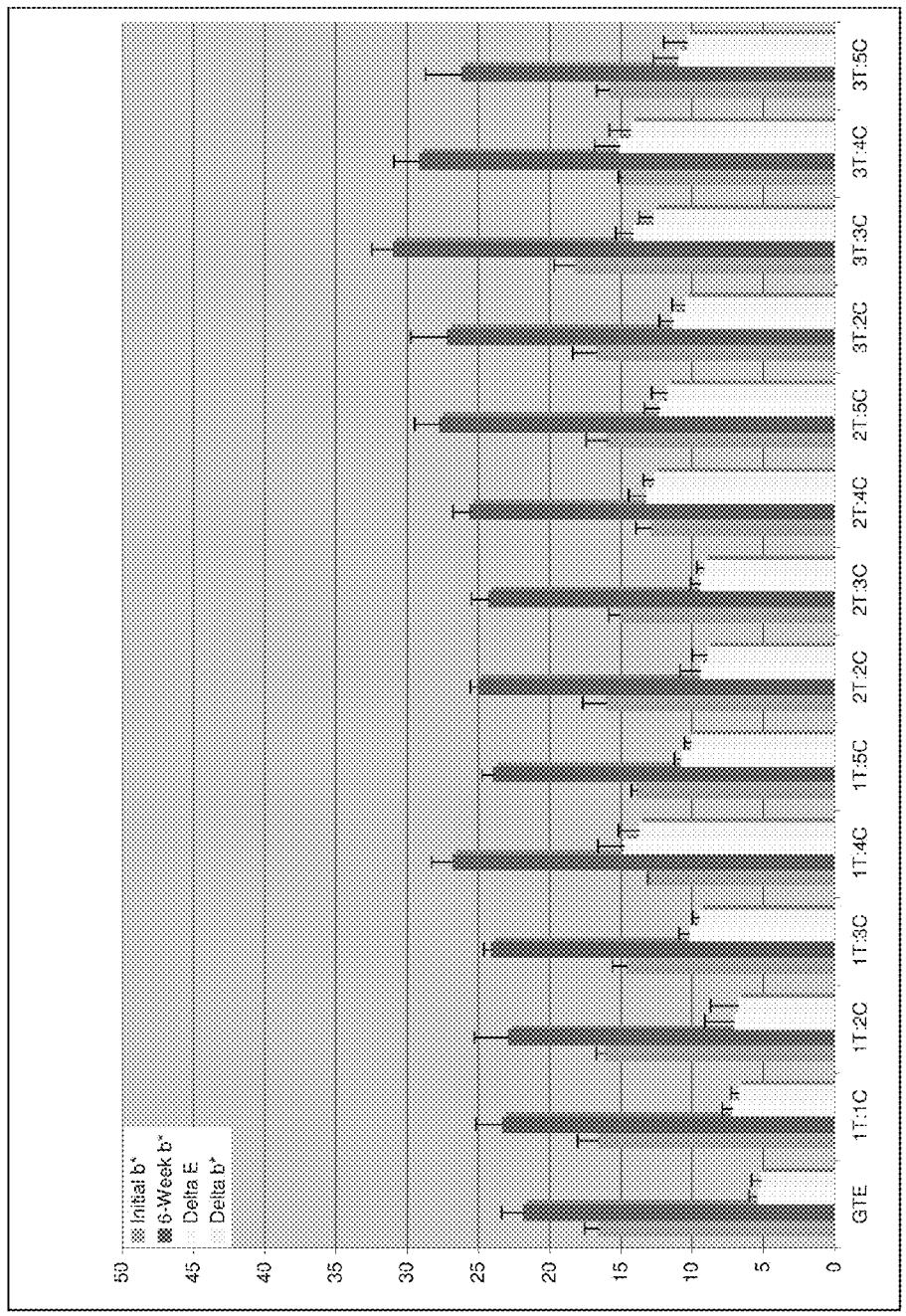
FIG. 35 illustrates the 6-week color stability of 50:50 dual-cure resins with 1% CQ and 2% DMAEMA

FIG. 35 illustrates a chart of initial and final (6-week) b* (yellowness), ΔE* and Δb* with respect to T:C ratio for 50:50 dual-cure resins with 1% CQ and 2% DMAEMA to illustrate color stability. While many of the experimental groups had lower initial b* than the light-cured GTE controls, none had lower final b* or better color stability (ΔE*and Δb*). Thus, further improvements are needed on the light-cure side using OPPI and the combination of 1T:3C was chosen due to its highest degree of cure.

Figure 36:
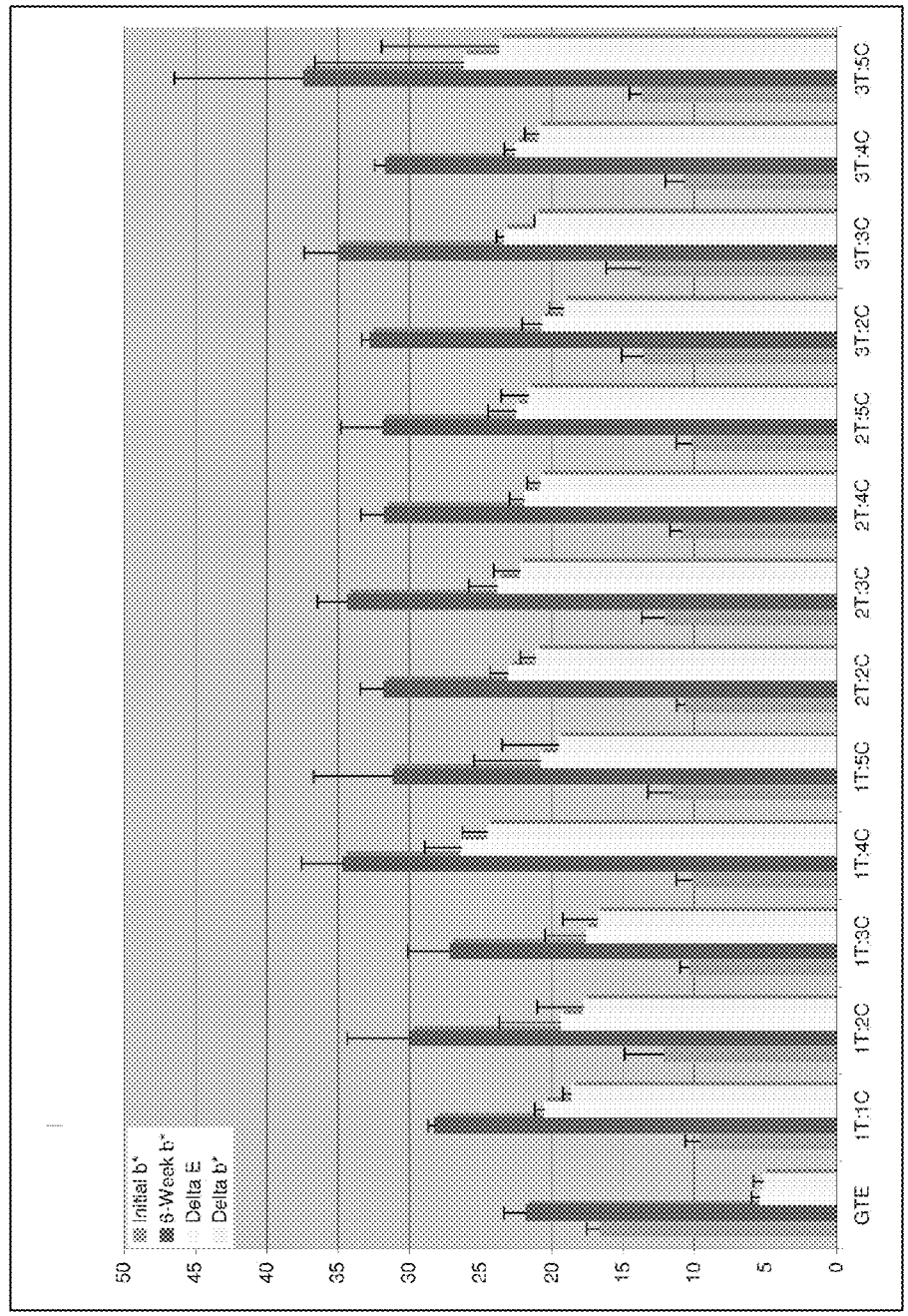
FIG. 36 illustrates the 6-week color stability of 75:25 dual-cure resins with 1% CQ and 2% DMAEMA

FIG. 36 illustrates a chart of initial and final (6-week) b* (yellowness), ΔE*and Δb* with respect to T:C ratio for 75:25 dual-cure resins with 1% CQ and 2% DMAEMA to illustrate color stability. While all of the experimental groups had lower initial b* than the light-cured GTE controls, none had lower final b* or better color stability (ΔE*and Δb*). In general, the final b* and hence color stability (ΔE*and Δb*) was worse than that of 50:50 dual-cure resins with CQ and DMAEMA. Thus, further improvements are needed on the light-cure side using OPPI, and the combination of 1T:3C was chosen due to its highest degree of cure.

Dual-cured resins using allyl thiourea and cumene hydroperoxide have increased degree of cure over light-cured GTE controls when used in a 50:50 (self-cure:light-cure) ratio but have equivalent or slightly reduced degree of cure when used in a 75:25 ratio. When cured in a 75:25 ratio, they can have lower initial color than conventional light-cured systems. 50:50 dual-cure resins also exhibited very low initial color for dual-cure resins. However, there was increased color shift after 6 weeks. Thus the addition of a low-color self-cure is not enough to produce a low-color, color-stable dual-cure resin. This was completely unexpected. The relationship between the self-cure and light-cure components is non-obvious and not additive.

Example 6

Issue 6 investigates the use of p-octyloxy-phenyl-phenyl iodonium hexafuoroantimonate (OPPI) in the light-cure side to further reduce color and improve color stability. The IT:3C self-cure formulation was chosen to do this due to the high degree of cure.

Issue 6

To determine the effect of p-octyloxy-phenyl-phenyl iodonium hexafuoroantimonate (OPPI), CQ and DMAEMA concentrations on degree of cure, color and color stability of dual-cure systems with a hydroperoxide oxidizing agent and substituted thiourea formulation chosen from ISSUE 5.

Methods

To the same monomer mixture and the 1T:3C self-cure formulation used in ISSUE 5 were added different concentrations of OPPI (0.5 & 1 wt %), CQ (0.5 & 1 wt %) and DMAEMA (0, 0.25, 1 & 2 wt %) in ratios of 50:50 or 75:25 (self-cure:light-cure). Various combinations were also formulated without the self-cure part and light-cured as controls. This mixture was light-cured into disc-shaped specimens ⅜" in diameter and ¹⁄₁₆" thick. After 24 hours, the samples were tested for hardness as a measure of degree of cure. Initial color and color stability in water at 60° C. for 6 weeks as done for ISSUE 5.

Results

Figure 37:
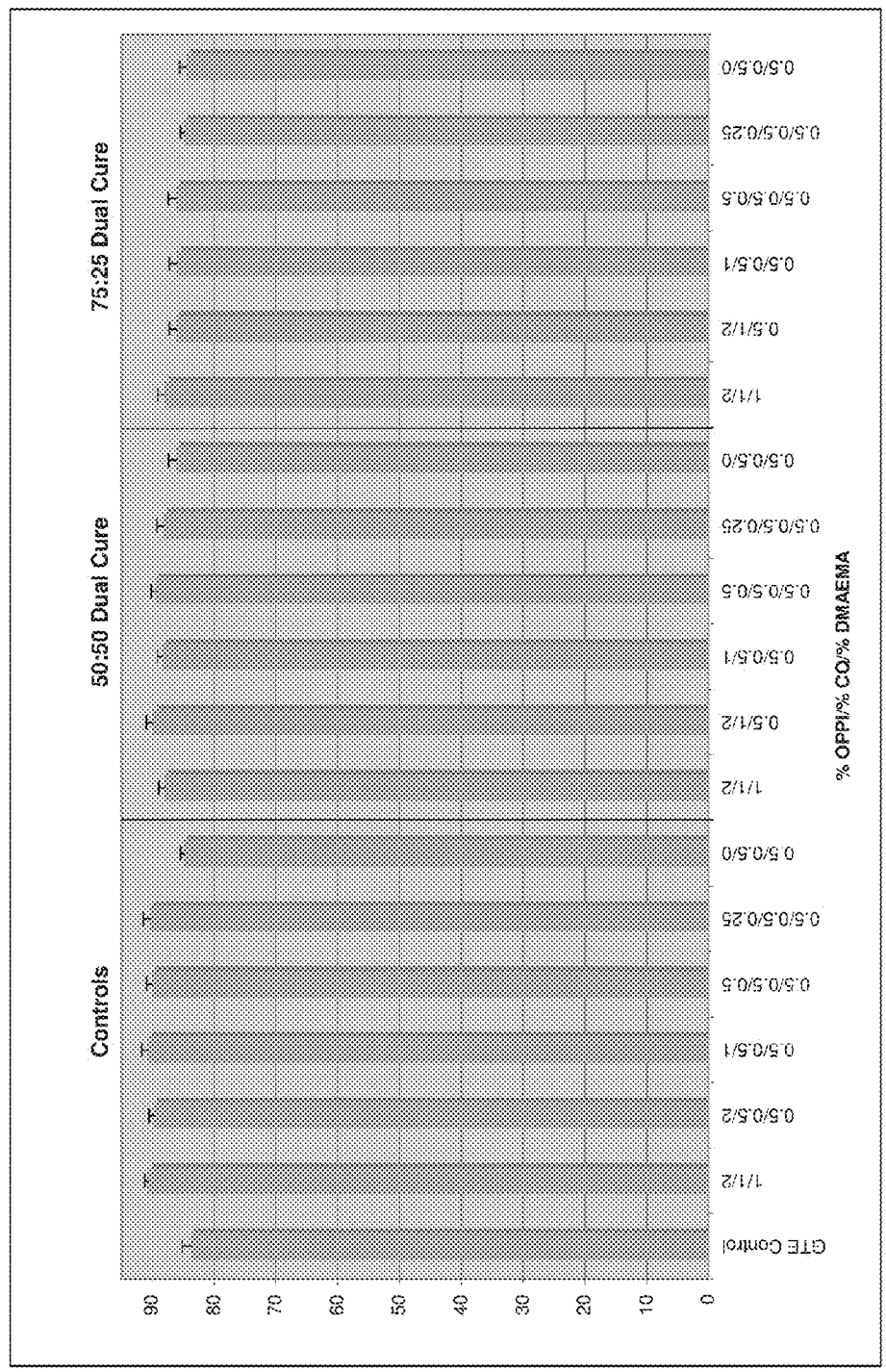
FIG. 37 illustrates the durometer hardness of dual-cure resins with 1-allyl thiourea (T):3 cumene hydroperoxide (C) and p-octyloxy-phenyl-phenyl iodonium hexafuoroantimonate (OPPI)

FIG. 37 illustrates a chart of the effect of varying OPPI (O), CQ and DMAEMA (D) concentrations on hardness and degree of cure of light-cure, and 50:50 and 75:25 dual-cure resins with 1T:3C. Most resins with OPPI had significantly higher degree of cure than light-cured GTE control. In general, a trend can be seen where the higher the self-cure component, the lower the degree of cure.

Figure 38:
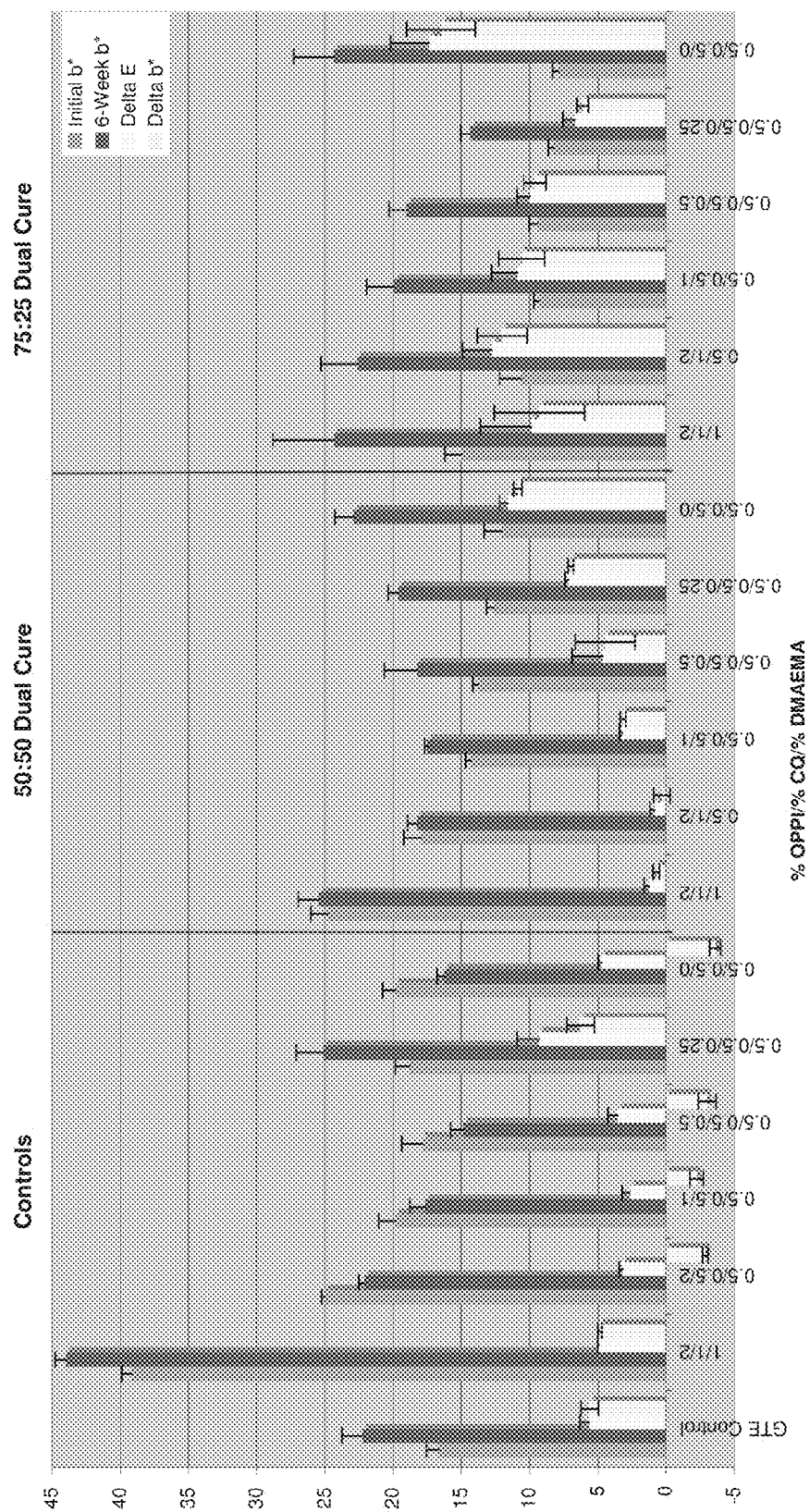
FIG. 38 is a chart of initial and final (6-week) $b^*$, $\Delta E^*$ (color shift) and $\Delta b^*$ (shift in yellowness) for 50:50 and 75:25 dual-cure resins with 1T:3C self-cure to illustrate the effect of OPPI, CQ and DMAEMA concentrations on initial color and color stability.

FIG. 38 illustrates a chart of initial and final (6-week) b* (yellowness), ΔE*and Δb* for 50:50 and 75:25 (self:light) dual-cure resins with 1T:3C self-cure to illustrate the effect of OPPI, CQ and DMAEMA concentrations on initial color and color stability. All dual-cures had very low initial and final b* for dual-cure resins. They were either comparable or lower than light-cured GTE. This is excellent considering that they are dual-cures and that dual-cures with CQ and DMAEMA in ISSUE 5 had much higher values 75:25 dual-cures had the lowest initial b* but highest color shift. Several control light-cure resins had negative Δb*, became less yellow and ended up giving the lowest final b*. However, 50:50 dual-cure resins had the four best color stable (ΔE*and Δb*) resins It is interesting that the reduction of DMAEMA, which is thought to reduce color, reduced initial b* but also reduced color stability. This might be due to a slight decrease in the degree of cure. Also, trends were very difficult to identify and the optimal combinations seem to go against the trend, which points to the synergistic relationship of the combinations. In fact, the group with the lowest color shift had the highest concentrations of CQ and DMAEMA.

All dual-cure resins had low color and increased color stability. They had lower initial b* than light-cured GTE controls and comparable final b*. 75:25 formulations had the lowest initial b* but highest color shift. Several 50:50 formulations produced the best performing samples with highest degree of cure, low initial b*, and least color shift.

These results demonstrate the concept that the combined use of OPPI and an organic hydroperoxide oxidizing agent plus a substituted thiourea formulation can significantly increase degree of cure, lower initial color and enhance color stability.

What is claimed is:

1. A hardenable composition comprising a light-curable component and a self-curable component, wherein said light-curable component comprises:
   an onium compound,
   a photosensitizer,
   and a resin system comprising a free radically active functional group and having no cationically active functional group, wherein said light-curable component is not miscible in water, and
   said self-curable component comprises a reducing agent and an oxidizing agent, wherein the reducing agent is selected from the group consisting of a urea reducing agent and a thiourea reducing agent,
   wherein the hardenable composition is formed by free radical polymerization of the resin system, and
   wherein the hardenable composition has an initial b* color value of less than 20 and a ΔE of less than 10, wherein ΔE represents the color change of the composition upon curing and is calculated using the equation $\Delta E=[(\Delta L^*)^2+(\Delta a^*)^2+(\Delta b^*)^2]^{1/2}$, and L* represents the lightness variable of the composition's color and a* and b* represent the chromatic characteristics of the composition's color in the CIE color system.

2. The hardenable composition of claim 1, wherein the light-curable component further comprises an amine co-initiator.

3. The hardenable composition of claim 1, wherein the photosensitizer comprises at least one component selected from the group consisting of 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3,3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, and acenaphthaquinone.

4. The hardenable composition of claim 1, wherein the onium compound is selected from the group consisting of p-octyloxy phenyl-phenyl iodonium hexafluoroantimonate (OPPI); tris(methylphenyl) sulfonium hexafluoroantimonate; diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; 4-isopropyl-4'-methyldiphenyliodonium tetrakis(pentafluorophenyl)borate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; diphenyliodonium hexafluoroantimonate (DPISbF$_6$); diaryliodoniun hexafluorophosphate; diaryliodonium hexafluoroantimonate; diphenyliodonium hexafluoroantimonate (DP), [4(1-octadecylphenoxyacetate)]phenyl iodonium hexafluoroantimonate (OPPA); and (4-octadecyloxyphenyl)phenyl iodonium hexafluoro hexafluoroantimonate (OPP).

5. The hardenable composition of claim 2, wherein the amine co-initiator is selected from the group consisting of 2-dimethylaminoethyl methacrylate (DMAEMA), ethyl 4-(N,N-dimethylamino)benzoate, N,N-dimethylaminoethyl methacrylate, dimethyl-p-toluidine, dihydroxyethyl-p-toluidine, N,N-cyanoethyl-methylaniline (CEMA), and combinations thereof.

6. The hardenable composition of claim 1, wherein the resin system comprises monomers of acrylate resins.

7. The hardenable composition of claim 1, wherein said oxidizing agent is selected from the group consisting of peroxides and salts thereof, hydroperoxides, transition metal compounds, perboric acid and salts thereof, permanganic acid and salts thereof, perphosphoric acid and salts thereof, and mixtures thereof.

8. The composition of claim 1, wherein the reducing agent is present in a first container and the oxidizing agent is present in a second container.

9. The composition of claim 8, wherein the first container contains at least one state selected from the group consisting of a paste, a liquid, a powder, and a gel.

10. A kit comprising one or more containers, wherein said one or more containers collectively contain said hardenable composition of claim 1.

11. The hardenable composition of claim 1, wherein said hardenable composition is used for at least one application selected from the group consisting of a dental adhesive, a dental cement, a dental composite, a tooth-colored filling, a luting resin, an esthetic veneer, a cavity base, a liner, a provisional restoration, and a fixed partial denture.

* * * * *